United States Patent
Spigelman et al.

[11] Patent Number: 6,119,033
[45] Date of Patent: Sep. 12, 2000

[54] METHOD OF MONITORING A LOCATION OF AN AREA OF INTEREST WITHIN A PATIENT DURING A MEDICAL PROCEDURE

[75] Inventors: Zachary S. Spigelman, Newton; Richard H. Theriault, Lincoln, both of Mass.

[73] Assignee: Biotrack, Inc., Cambridge, Mass.

[21] Appl. No.: 08/880,477

[22] Filed: Jun. 23, 1997

Related U.S. Application Data

[60] Provisional application No. 60/039,285, Mar. 4, 1997.

[51] Int. Cl.[7] .................................................... A61B 5/00
[52] U.S. Cl. ........................................... 600/426; 427/429
[58] Field of Search ..................... 600/425–427, 600/429, 407, 431, 414, 417, 411; 606/130

[56] References Cited

U.S. PATENT DOCUMENTS

| | | | |
|---|---|---|---|
| 5,042,486 | 8/1991 | Pfeiler et al. | 128/653 R |
| 5,279,309 | 1/1994 | Taylor et al. | 128/782 |
| 5,377,678 | 1/1995 | DuMoulin et al. | 128/653.1 |
| 5,386,447 | 1/1995 | Siczek | 378/37 |
| 5,577,502 | 11/1996 | Darrow et al. | 128/653.1 |
| 5,647,373 | 7/1997 | Paltieli | 128/749 |

FOREIGN PATENT DOCUMENTS

| | | |
|---|---|---|
| 0 600 610 A2 | 8/1994 | European Pat. Off. . |
| 2 719 760 | 11/1995 | France . |
| 39 02 249 A1 | 2/1990 | Germany . |
| 42 25 112 C1 | 9/1993 | Germany . |
| 44 18 868 A1 | 11/1995 | Germany . |
| WO 93/14712 | 5/1993 | WIPO . |
| WO 94/23647 | 10/1994 | WIPO . |
| WO 96/11624 | 4/1996 | WIPO ..................................... 600/426 |
| WO 97/03609 | 2/1997 | WIPO . |
| WO 97/29682 | 8/1997 | WIPO . |

*Primary Examiner*—Ruth S. Smith
*Attorney, Agent, or Firm*—Wolf, Greenfield & Sacks, P.C.

[57] ABSTRACT

Methods and apparatus for a medical imaging system are disclosed. The imaging system is particulary suited for surgical procedures performed with respect to a lesion in a breast, although application of the invention is not so limited. An image of a portion of a patient's anatomy can be displayed on a computer. A surgical instrument and a lesion within the patient's anatomy can be displayed, showing the relative positions of each. A portion of the patient's anatomy can be monitored using markers or sensors that report position relative to an external reference point. Movement of a lesion within soft tissue can be calculated and displayed in response to changes in position or shape of the soft tissue. Accordingly, position of a lesion within a breast can be tracked in response to changes in the shape of the breast as the patient is moved or the breast is manipulated during the procedure. The system can show multiple views, can appropriately magnify the view when the instrument is in a critical position and can provide other signals assisting a surgeon in performing a procedure. Sensors and instruments for use in the system are disclosed. The procedure can be recorded for playback.

13 Claims, 10 Drawing Sheets

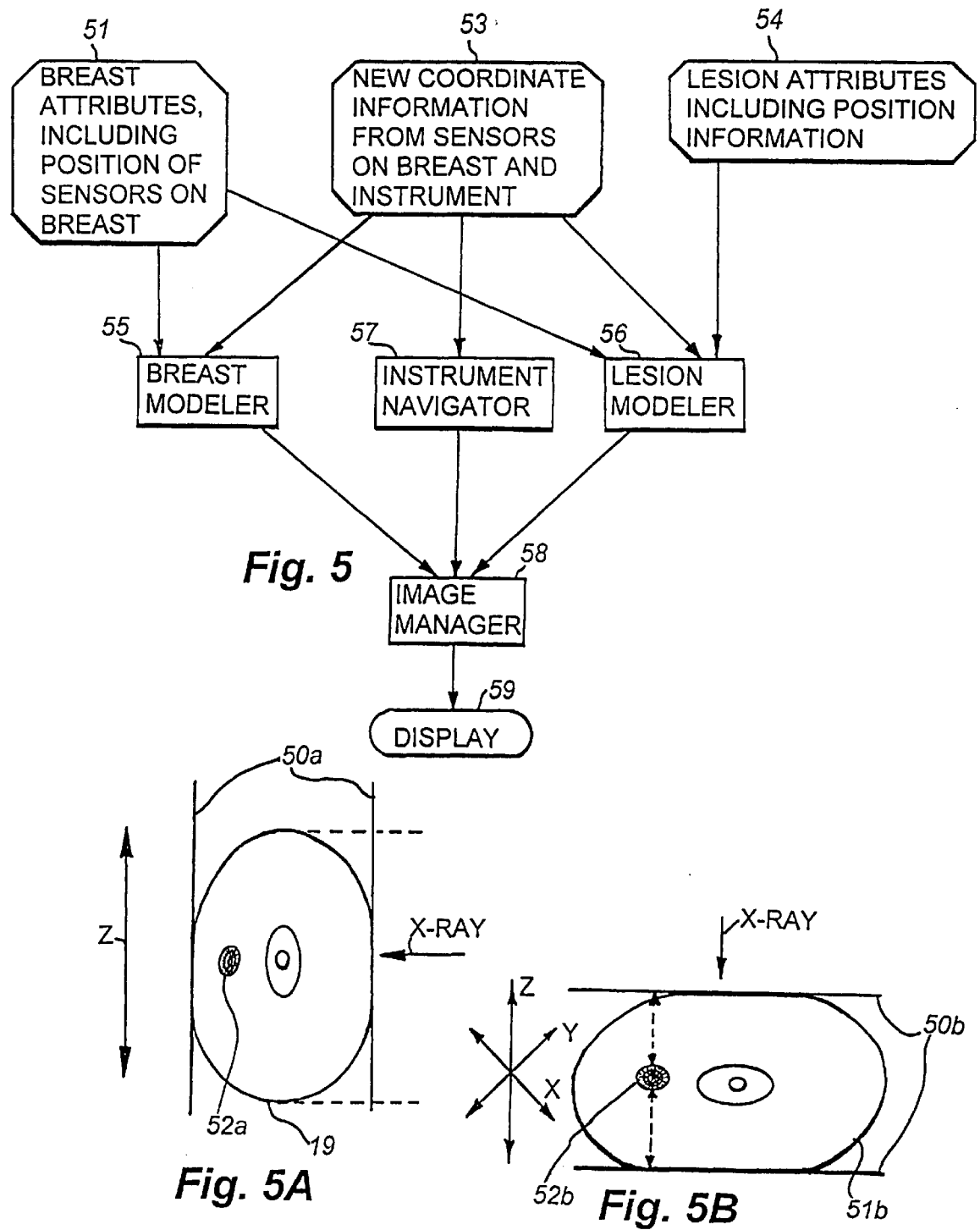

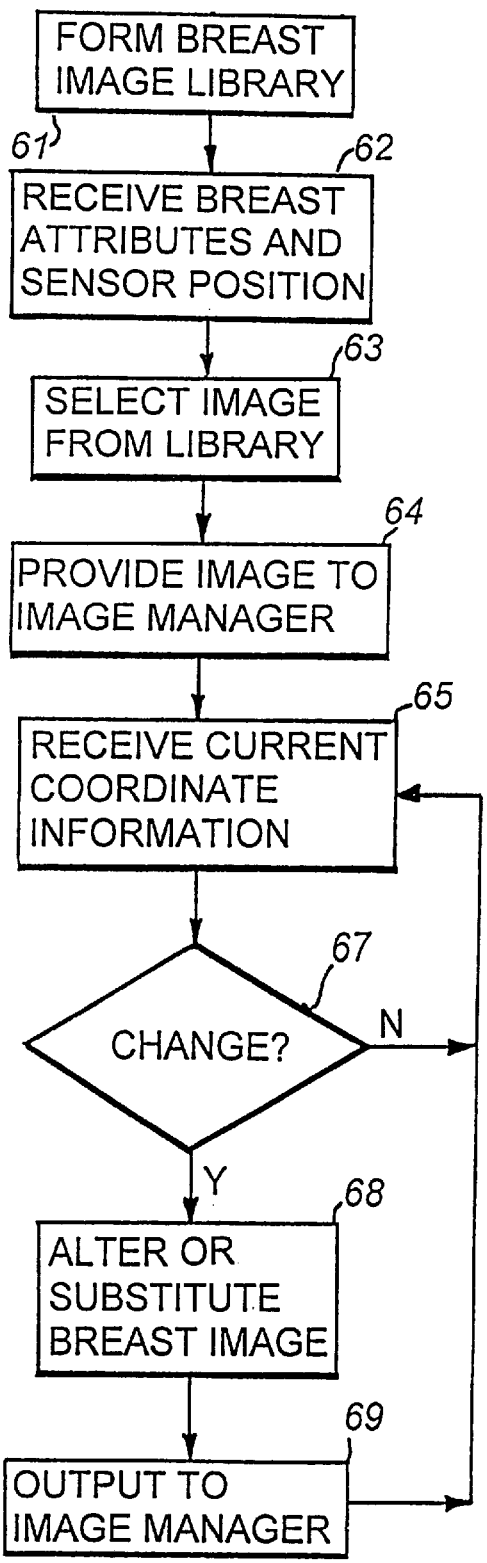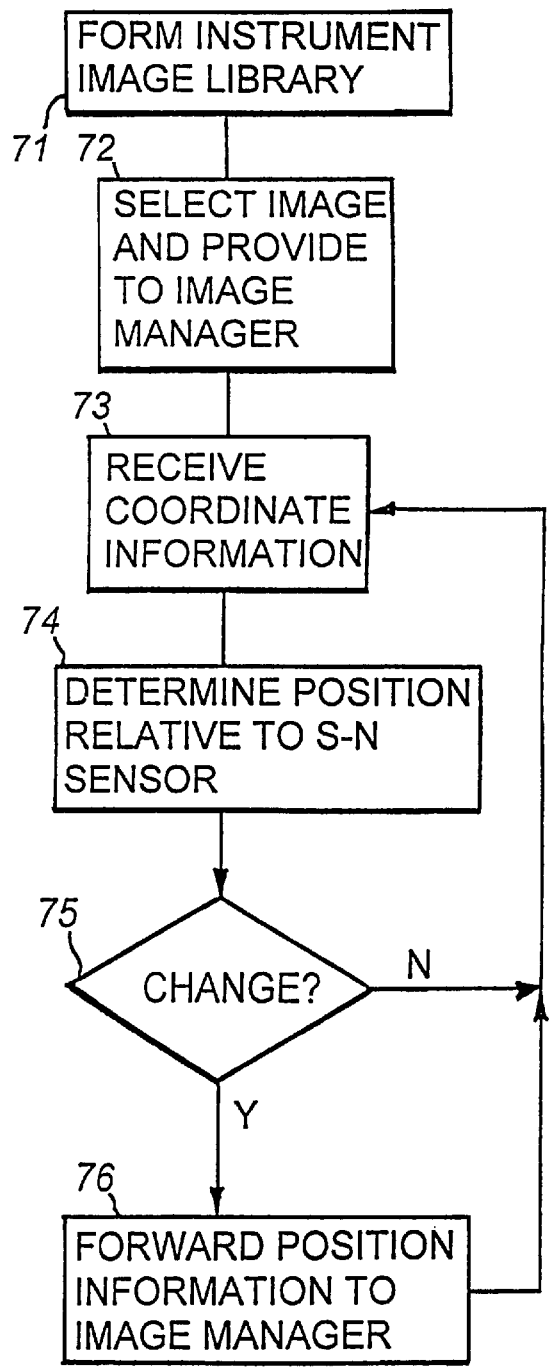
Fig. 6
Fig. 7

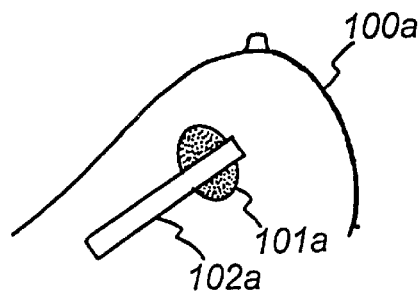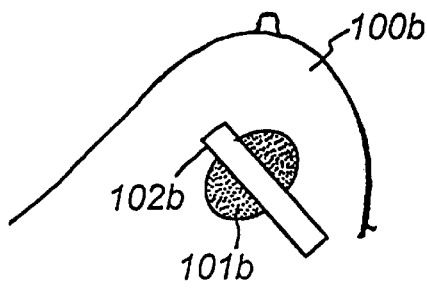
Fig. 10A  Fig. 10B
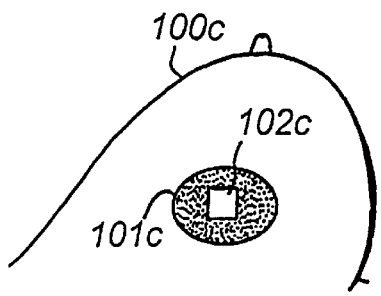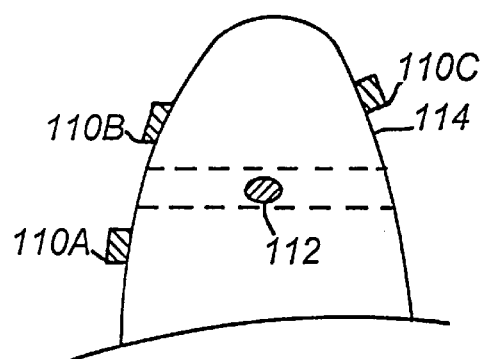
Fig. 10C  Fig. 11
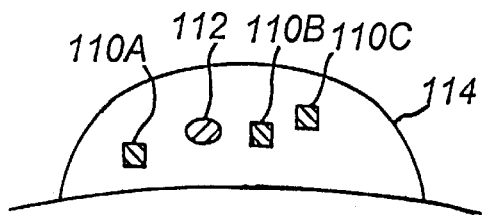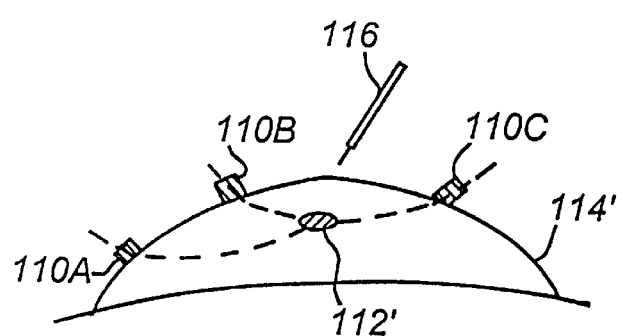
Fig. 12  Fig. 13

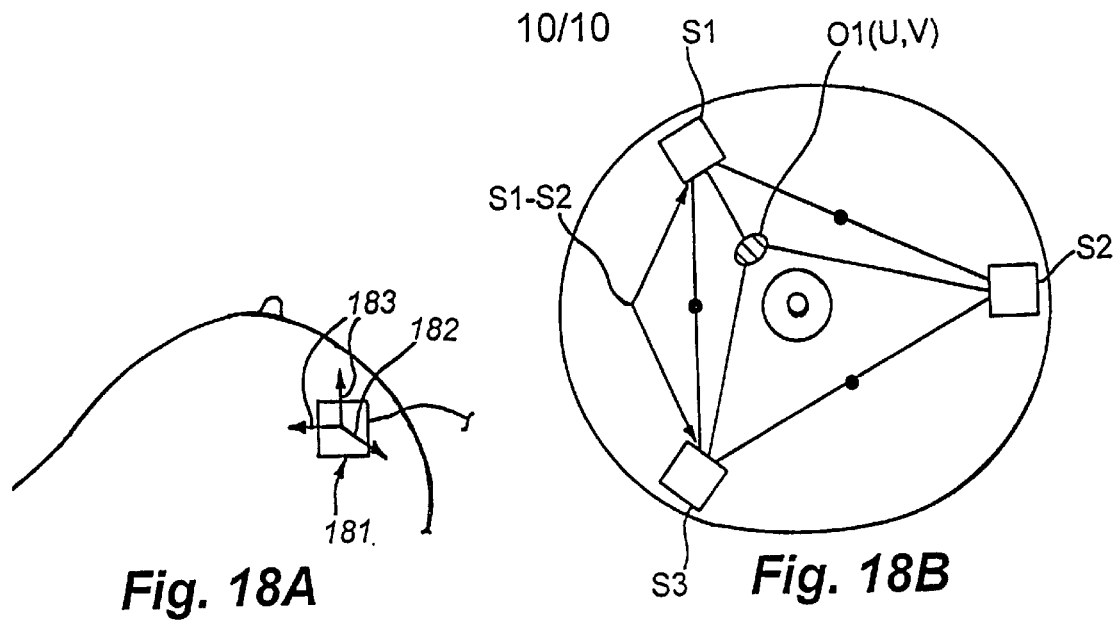
Fig. 18A
Fig. 18B
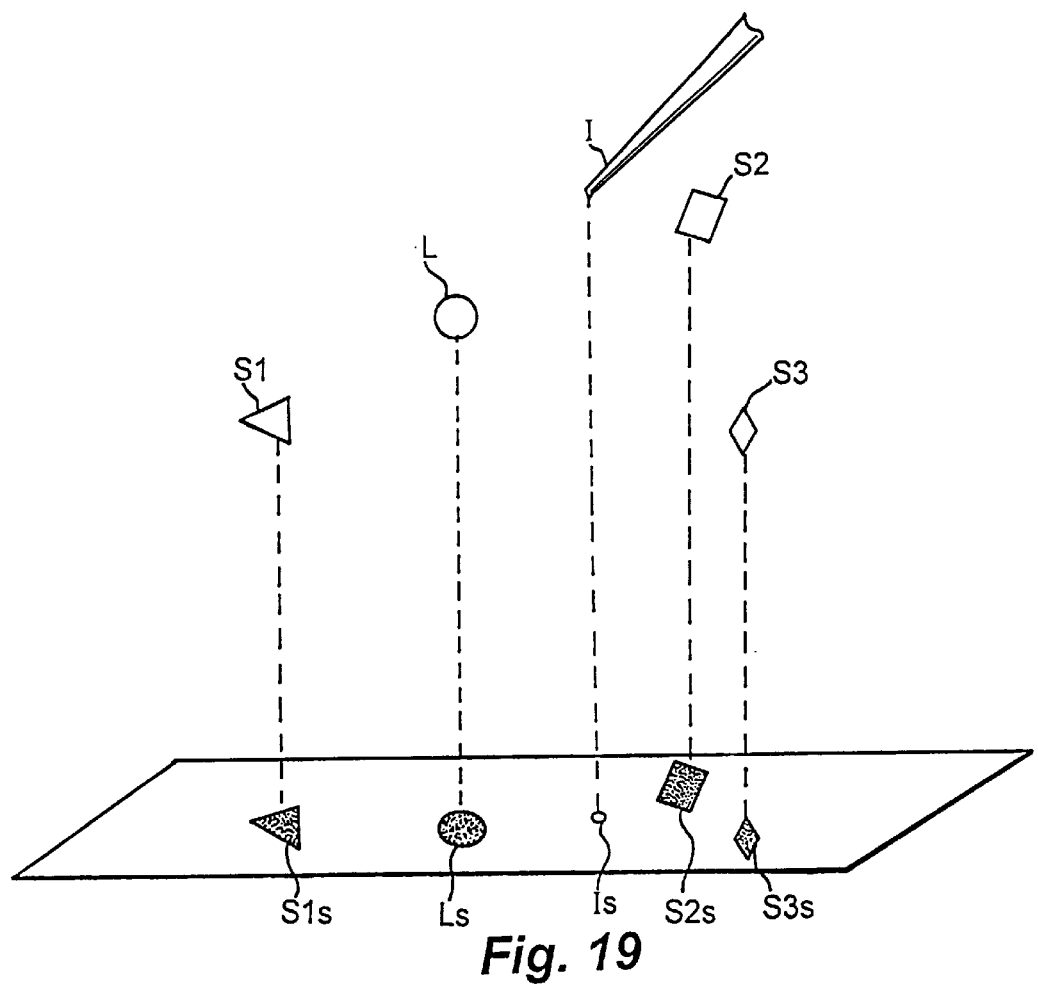
Fig. 19

METHOD OF MONITORING A LOCATION OF AN AREA OF INTEREST WITHIN A PATIENT DURING A MEDICAL PROCEDURE

CROSS REFERENCE

We claim, under 35 U.S.C. § 119(e), the benefit of provisional application serial No. 60/039,285 entitled MEDICAL SENSING AND IMAGING SYSTEM, filed on Mar. 4, 1997.

FIELD OF THE INVENTION

The present invention relates generally to methods and apparatus for medical sensing and imaging. More particularly, the present invention relates to methods and apparatus for sensing and imaging anatomy and surgical instruments during a surgical procedure.

DESCRIPTION OF THE RELATED ART

The present invention relates generally to medical imaging and sensing of anatomical features and surgical instruments. The invention will be described in the context of medical imaging for surgical procedures to be performed on a woman's breast, and more particularly related to biopsies and surgical removal of a cancerous lesion within a breast. This is not, however, intended to be limiting.

Mammography is the primary method for screening for breast cancer. The primary role of mammography is to screen asymptomatic women in order to detect breast cancer at an earlier stage than would occur with only self-examination and/or clinical breast examination. Detection at an earlier stage of the disease has been shown to reduce or delay mortality from breast cancer.

Mammography uses X-rays to create an image of the interior of the breast. Mammography typically requires careful positioning of the patient by a highly skilled technician trained in mammographic technique. Optimum results depend on pulling and squeezing of the breast during the mammogram, which can be painful. Accurate results are also highly dependent on interpretation of films by a radiologist.

When a patient is screened by mammography, a "suspicious mass" or lesion is often identified. In these cases, it must be determined whether the lesion is cancerous. This often requires that a piece of the lesion be removed for further investigation. To do this, of course, there must be some way that a surgeon can find the lesion in the breast (referred to as "tumor localization").

A biopsy is a procedure for removing a portion of the lesion for the purpose of determining whether the lesion is malignant. There are at least three methods of biopsy: surgical biopsy, core biopsy and fine needle (aspiration) biopsy.

For surgical biopsy, lesion location can be established through a procedure called needle localization. Needle localization begins when a specially trained technician puts the breast into a specialized mammography fixture. Several views of the breast are taken using stereotactic mammography to determine the approximate location of the "suspicious mass." A needle is placed into the breast toward the lesion. The placement of the needle is verified through mammography. The needle insertion and verification are repeated until the placement is deemed appropriate by a radiologist. A small wire with a J hook is then placed through the core of the needle. The needle is removed and the wire remains. At this point, the needle localization procedure is complete. The patient is then moved to a surgical setting. During surgery, the wire is used as a guide for the surgeon to cut to the "suspicious mass." When the surgeon reaches the area where the wire terminates, a tissue sample is taken. The sample is verified to be that of the identified "suspicious mass" by comparing a mammogram of the tissue sample with that of the original mammography.

In practice, depending on breast size, however, there is often a ½ inch movement of the wire before or during the procedure. Accordingly, the sample tissue may not have come from the "suspicious mass." In those cases, the surgeon searches around the wire termination point and repeats the sample and verification procedure until a match is found. Mammography is used repeatedly in many aspects of breast cancer screening and diagnosis. For example, a dozen mammographic X-rays may be required in support of a single surgical biopsy.

In core biopsy procedures, a tool is positioned within the breast. The breast is then imaged to determine location of the tool with respect to the lesion. The tool may then be repositioned to more closely target the lesion. This process can be cumbersome and require multiple images of the breast.

In many cases, where the lesion is determined to be cancerous, the lesion must be surgically removed. When the breast is largely preserved and only the lesion removed, the procedure is called a lumpectomy. A lumpectomy sometimes requires needle localization as described above. Instead of taking a piece of the "suspicious mass" for analysis, however, the entire mass is surgically removed.

Because the wire may move during or before the procedure, the biopsy and excision procedures often target the suspicious mass inaccurately. As a result, the procedures are both lengthier than would otherwise be required, occasionally unsuccessful due to failure to accurately localize the lesion, and may result in the unnecessary removal of healthy tissue from the breast.

SUMMARY OF THE INVENTION

The invention provides improved methods and equipment for sensing, and for imaging, during surgical procedures.

According to one embodiment of the invention, a method of monitoring a portion of a patient's anatomy during a surgical procedure is disclosed. According to this embodiment, at least one marker is affixed to the surface of the patient's skin in the area of said anatomy portion and the position of the marker is monitored relative to the identified position of a lesion. The marker may be a position-reporting sensor. The method may further include steps of displaying on a screen a surgical instrument to be used in the procedure and a lesion within the portion of the patient's anatomy. The method may be applied, for example, to sensing and imaging of procedures performed with respect to a lesion within a breast. According to another embodiment of the invention, a system is provided to facilitate and perform this method.

According to another embodiment of the invention, a sensor unit is disclosed for use in a medical monitoring system during a surgical procedure performed on a patient. In this embodiment, the sensor unit comprises a position-reporting sensor together with means for affixing the sensor to a patient's skin.

According to another embodiment of the invention, a method for monitoring a location of an area of interest within a patient is disclosed. According to this embodiment, a plurality of markers are affixed to the skin of the patient, the markers being capable of movement relative to each other as the skin moves. Changes in the position of the markers are monitored and a new location of the area of interest can be determined by reference to the changed positions of the markers.

According to another embodiment of the invention, a method of monitoring a location of a lesion within a breast having a shape is provided. According to this embodiment, the method includes the steps of localizing the position of the lesion within the breast, monitoring changes in the shape of the breast and determining a new location of the lesion based on changes in the shape of the breast. According to another embodiment of the invention, a system is disclosed for performing this method.

According to another embodiment of the invention, a surgical instrument for use with the medical imaging system is disclosed. The surgical instrument includes an operating portion to be used to affect a surgical procedure and a position-reporting sensor disposed on the surgical instrument.

According to another embodiment of the present invention, an image library for use in a medical imaging system is disclosed. The image library includes a digital storage medium to store at least one record of a three-dimensional image of a surgical tool.

According to another embodiment of the invention, a method of affixing a plurality of markers to a breast for use in a surgical procedure performed on a lesion within the breast is disclosed. According to this embodiment, the location of the lesion within the breast is determined. Positions to locate the markers are then calculated, to reduce interference with the surgical procedure and to increase effectiveness of the markers. The markers may then be affixed at the calculated positions.

According to another embodiment of the present invention, a method of reviewing a surgical procedure performed on a portion of a patient's body is disclosed. According to this embodiment, the positions of the surgical instrument and the portion are monitored electronically during the procedure. This information is stored digitally and used to display an image corresponding to the performed procedure. According to another embodiment of the invention, a system for performing this method is disclosed.

According to another embodiment of the present invention, a method of imaging a surgical procedure is disclosed. According to this embodiment, an image of an area of interest within a patient is displayed. An image of an operating portion of a surgical instrument is also displayed, showing the physical location of the operating portion to the area of interest. On the display, the part of the operating portion that is located within the area of interest is distinguished from parts of the operating portion that are not within the area of interest. According to another embodiment of the invention, a system is disclosed to perform the above method.

According to another embodiment of the invention, a method of imaging a surgical procedure is disclosed. According to this embodiment, an image of an area of interest within the patient is displayed. (When reference is made herein to an image of an object, unless stated otherwise, this includes both an actual image of the object and, as an alternative, an image corresponding to the object, even if the corresponding image was not obtained through photography or another direct imaging technique (e.g., a corresponding image drawn by an artist or produced by a computer).) An image of an operating portion of the surgical instrument is also displayed. The method includes a step of indicating when the operating portion is located proximate to the central part of the area of interest. This method may be applied, for example, to indicate when the tip of a biopsy tool is located within the center of a lesion within a breast. According to another embodiment of the invention, a system for performing this method is disclosed.

In another embodiment, a signal may be provided to indicate when the surgical tool is near an area of the patient's anatomy that should be avoided. For example, a warning signal could indicate that a scalpel is getting dangerously close to a major blood vessel.

Whether the signal is used to indicate that the surgical instrument is in the appropriate position or is near an area of the patient that should be avoided, the signal may be audible, so that the surgeon becomes aware that the surgical instrument is in a certain position, even when the surgeon is not looking at a display screen. An audible (or visual) signal can vary in amplitude based on proximity to the area of interest (e.g., a targeted lesion or blood vessel to be avoided), thus providing additional information to the surgeon.

In another embodiment of the invention, for procedures where a tool needs to be positioned in a certain location within a patient, a display can provide other information about the position of the tool. For example, the display can indicate the current direction of the tool with respect to the area of interest, assuming that the tool were slid straight into the patient, based on its current orientation.

According to another embodiment of the present invention, a method of performing a lumpectomy on a lesion within a breast, using a scalpel, is disclosed. According to this embodiment, an image of the lesion is displayed. An image of the blade of the scalpel is also displayed, so as to distinguish that portion of the displayed image of the blade that is within the lesion from that portion that is not within the lesion. Surgical cuts may then be performed around the lesion using the blade, when the cutting portion of the blade is not distinguished as being within the lesion.

According to another embodiment of the present invention, a method of providing a medical image of a portion of a patient's anatomy is disclosed. According to this embodiment, a set of images of the portion is provided, the set of images being derived separate from the patient. At least one attribute of each of the images is determined, and a corresponding attribute is determined for the patient. At least one image is selected from the set of images based on the attributes of the selected image and the portion of the patient. According to another embodiment of the present invention, a system is provided to perform this method.

Other aspects and advantages of the present invention will become apparent from the detailed description provided herein.

BRIEF DESCRIPTION OF THE DRAWINGS

FIG. 5A illustrates taking of a mammography of a breast in a first direction.

FIG. 5B illustrates taking of a mammography of a breast in a second direction.

FIG. 5 illustrates a block diagram of one embodiment for operation and implementation of a medical assistant computer used in a medical sensing and imaging system.

FIG. 6 illustrates one method for implementing a breast modeler for use in a medical assistant computer.

FIG. 7 illustrates one method for implementing the function of an instrument navigator in a medical assistant computer.

FIG. 10A illustrates an embodiment of a targeting display indicating error in the aiming of a surgical tool.

FIG. 10B illustrates an embodiment of a targeting display indicating error in the aiming of a surgical tool.

FIG. 10C illustrates an embodiment of a targeting display indicating when the aiming of a surgical tool is correct.

FIG. 11 illustrates a graphic rendition of a mammography of a breast in a first direction.

FIG. 12 illustrates a graphic rendition of a mammography of a breast in a second direction.

FIG. 13 illustrates a two dimensional display according to one embodiment of the present invention.

FIG. 18A illustrates the tangent plane and normal vector for a sensor on a breast.

FIG. 18B illustrates computation of barycentric coordinates of a lesion on a spline defined by sensors and the lesion.

FIG. 19 illustrates an embodiment of a display according to the present invention.

DETAILED DESCRIPTION

In one aspect of the invention, improvements are made to procedures for examining and removing lesions within a breast. Application of the invention, however, is not so limited. Various features of the invention may be applied to sensing or imaging any soft organ or tissue, imaging hard features, and imaging external as well as internal features. Certain embodiments of the invention are particularly well suited for imaging a portion of the body that is composed primarily of soft tissue, where the soft tissue can move in response to movement of other anatomical features (such as a lesion within a breast moving in response to movement of the skin of the breast, when the shape of the breast is changed through manipulation). While the detailed description presents the invention in the context of procedures for examination or removal of a lesion within a breast, this is not intended as limiting.

While the invention is also described with reference to X-ray localization of tumors, this is not intended as limiting. MRI technology, computer tomography, ultrasound and other diagnostic internal imaging techniques may be used in the context of breast cancer diagnosis and treatment as well as in other applications.

General Procedure

Figure 1:
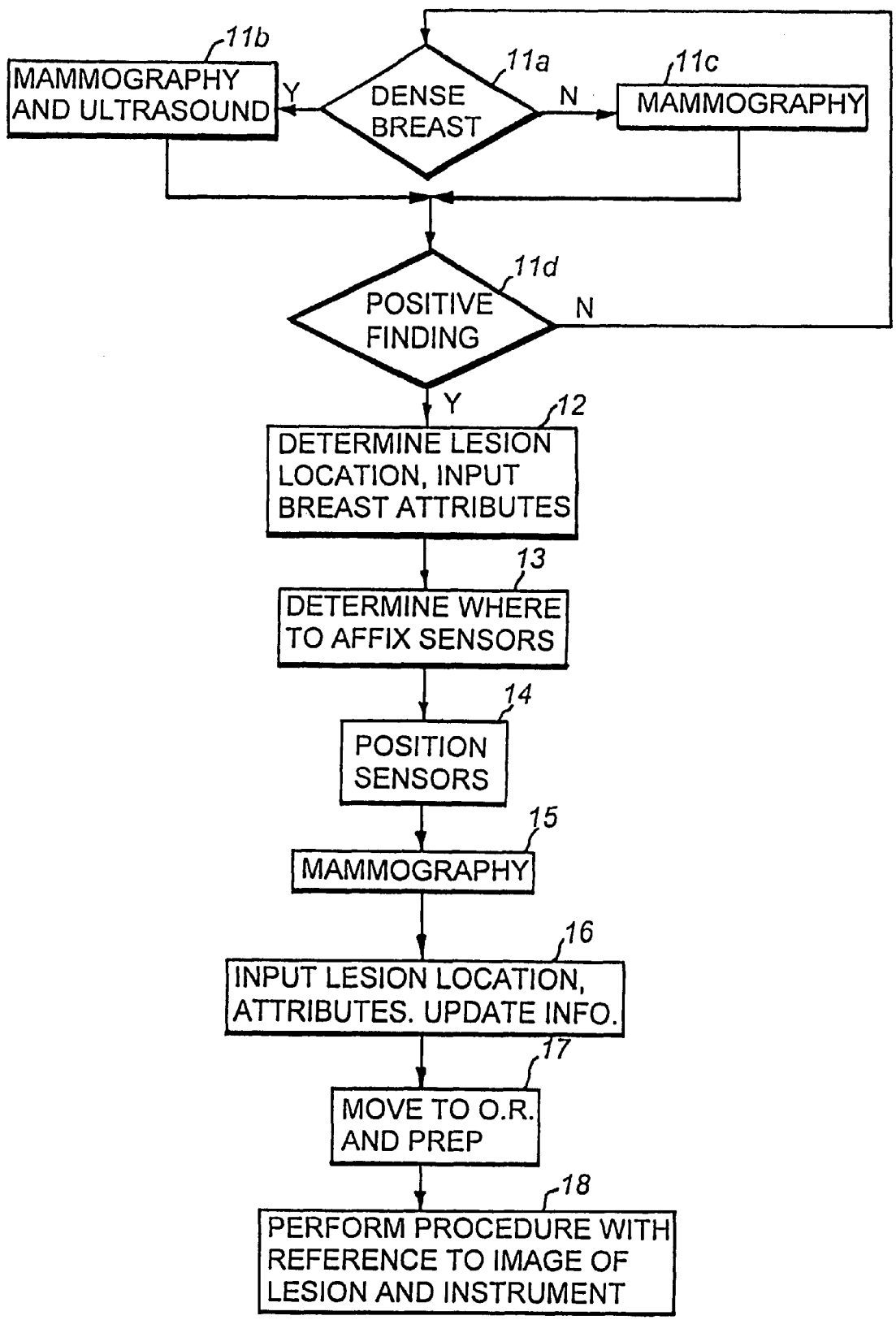
FIG. 1 illustrates one embodiment of a method for medical sensing and imaging of a breast during a surgical procedure.

FIG. 1 illustrates an embodiment of a procedure according to the present invention and performed with reference to a lesion within a breast. Steps 11a–11d relate to general screening of female patients for lesions within a breast, as known in the art. At step 11a, the screening process begins. At step 11a, it is determined whether the breast is composed of dense tissue. If the breast is dense, at step 11b, screening is performed using both mammography and ultrasound, as known in the art. If the breast is not dense, screening is done only with mammography, at step 11c.

At step 11d, the results of mammography, and in the case of a dense breast also the ultrasound, are examined to determine whether there is a positive finding. In this case, a positive finding indicates that a potentially malignant lesion is within the breast.

If there is a positive finding, at step 12, the approximate lesion location is determined and input to a medical assistant computer. The medical assistant computer may be a general purpose computer, such as a Pentium-based personal computer, programmed to perform the functions described below. Special purpose hardware, other computers or some combinations of these may, of course, be used instead.

The approximate lesion location may be determined from the screening mammography or from a new mammography, either by medical personnel or by scanning the X-rays into the medical assistant computer and having the computer automatically determine lesion location. In one embodiment, the location of the lesion is specified only by the quadrant of the breast in which the lesion is located. Of course, more accurate lesion location measurements could be used.

At step 12, breast and lesion attributes may also be input to the medical assistant computer (or determined by the medical assistant computer by scanning the X-rays). Examples of attributes and how they can be measured and input or stored are described in greater detail below.

At step 13, the lesion location information, and potentially the breast and/or lesion attribute information, is used by the medical assistant computer to compute locations on the breast to affix markers. The markers are used to monitor movement of the breast and changes in the shape of the breast, for example when the breast is manipulated during surgery or during a mammography. The markers and their operation are described in greater detail below. The medical assistant computer calculates marker location so that the calculated position reduces interference of the markers with the surgical procedure to be performed, also described in greater detail below.

At step 14, the markers are positioned on the breast, in accordance with the position determined by the medical assistant computer, discussed in greater detail below. (In other embodiments, the marker locations can be marked on the patient and the actual markers affixed later in the procedure.)

At step 15, a new mammography is taken. This mammography is also taken in accordance with the general procedure known in the art. Two plates, including fenestrations, are positioned vertically on either side of the breast and a first X-ray is taken. The plates are then positioned horizontally and on either side (top and bottom) of the breast and a second X-ray is taken. The location of the lesion can be isolated in three-dimensional space using the two (two-dimensional) X-rays. The fenestration markers on the plates are used as a framework for specifying location. The location of the markers is also known, relative to the fenestrations. Accordingly, the location of the lesion relative to the markers can be determined. This process is described in greater detail below.

At step 16, the lesion location is input to the medical assistant computer. Lesion location can be input in the form of the fenestration readings from the X-rays. The fenestration location of the markers may also be input (although this may be unnecessary if the medical assistant computer calculated and specified the fenestration locations where the markers should be affixed, as described below).

At step 16, lesion attributes may also be input. Such attributes are described in greater detail below.

In another embodiment, the X-rays may be digitally scanned and the medical assistant computer can automatically determine the lesion location and attributes.

At step 17, the patient is moved to a procedure room with the breast markers in place. At this location, the procedure will be performed. The patient is prepared in a sterile manner. The markers are maintained in place during preparation for the procedure.

At step 18, the procedure is performed with reference to the image of the instrument and lesion on a video screen. As described in greater detail below, the video screen of a medical assistant computer displays an image of the instrument and an image corresponding to the lesion. The surgeon may then perform the procedure, looking at the video screen of the medical assistant computer to determine the location of the instrument relative to the lesion.

With reference to a lesion located within a breast, the procedure may be, for example, a biopsy or lumpectomy. As would be apparent to one of skill in the art based on the disclosure provided herein, the imaging disclosed herein can be used to increase the chance that a biopsy selects tissue from the area of interest. The procedure may also be used to increase the likelihood that the entire malignant lesion is removed during a lumpectomy. Viewing of the video display may also permit a surgeon to remove smaller amounts of healthy tissue during a lumpectomy.

The above technique may also be used for needle localization during a surgical biopsy. In this case, for example, the image may be used for placement of a J hook needle prior to a surgical biopsy. If the needle becomes displaced during the procedure, it can be repositioned with reference to the image on the video display. This avoids the need to take new X-ray images to reposition the needle.

The above technique may also be used to supplement existing techniques. For example, standard needle localization procedure can be employed in addition to the assistance provided by the medical imaging system. This would permit surgeons to rely on familiar procedures, while also deriving the benefits of the medical imaging system. Again, if the needle becomes displaced during the procedure, the surgeon could use the medical imaging system to reposition the needle without the need for taking a new set of X-rays.

Application of the present invention may also be found in other surgical contexts, laproscopic surgery being just one example.

Medical Assistant Computer System

Figure 2:
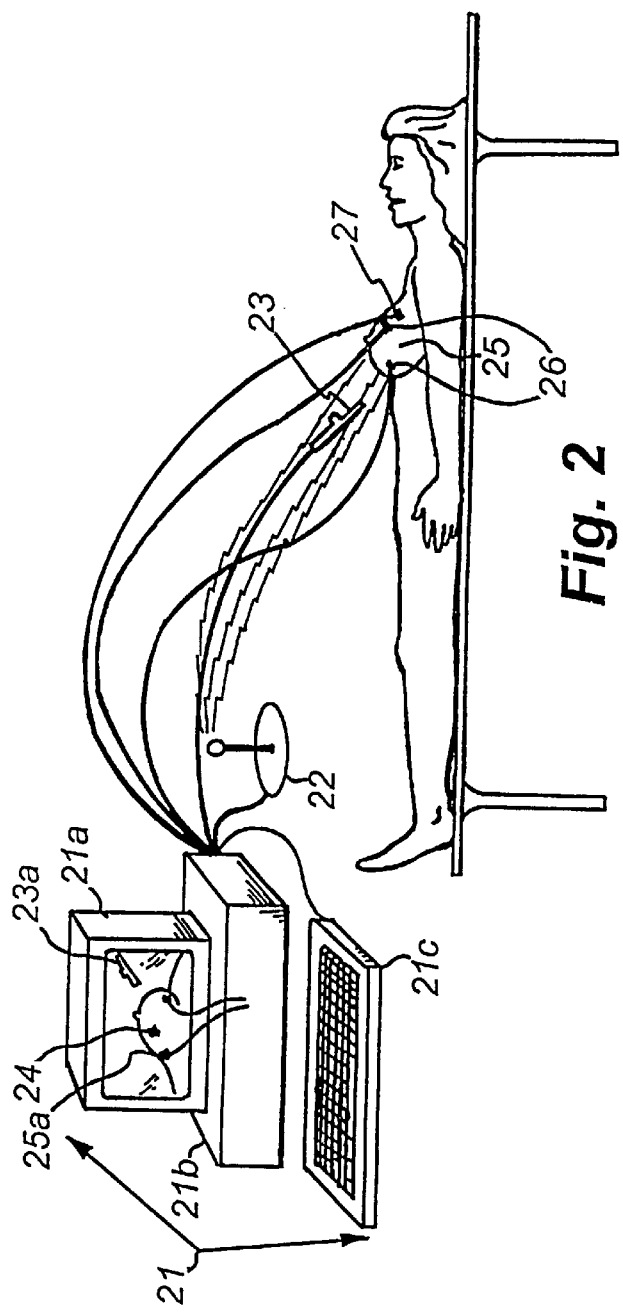
FIG. 2 illustrates a medical sensing and imaging system for use during a surgical procedure performed on a breast.

FIG. 2 illustrates one embodiment of the present invention, at the system level. A medical assistant computer 21 is used to display images 25a corresponding to the patient's breast, a surgical instrument 23a used for the surgical procedure and the lesion 24 located within the breast. As described above, the medical assistant computer may be a general purpose computer such as a microcomputer with an Intel Corporation Pentium processor programmed to perform the methods described herein. As described above, the medical assistant computer could also be implemented in special purpose hardware or software running on other types of computers, or other combinations as known to one of skill in the computer arts. The medical assistant computer used to view the images of the breast, lesion and instrument may be the same computer as is used to determine the best location of the sensors on the breast, as described generally above. In the alternative, of course, separate computers may be employed.

The medical assistant computer includes a CRT display 21a, preferably in color, a processing unit 21b and a keyboard input device 21c. Of course, variations of the configuration of such computer are well known in the art. As one example, other input devices may be used, such as a mouse.

Markers

In one embodiment, the markers on the patient's breast are used to provide position information about each marker. For example, the markers may be "position-reporting sensors" that include transmitters to transmit a signal from which position information can be derived by a receiver 22 (these are included in the term "sensor" as used in this specification; although some such devices arguably do not "sense" anything because they simply broadcast positional information, their ultimate function is for sensing the position of the surface to which they are affixed). In another embodiment, a transmitter 22 generates a magnetic (or other) field which is sensed by position-reporting sensors 26 that include a sensor to sense the field and a transmitter (not shown) to report this information (e.g., over a wire) to hardware, associated with the medical assistant computer, which converts that signal to digital positional information. Other markers may be used, so long as positional information may be determined. Such markers may use magnetic, electric, optical, infra-red, microwave, RF or any other technology to derive position information. While the remainder of the detailed description assumes use of position-reporting sensors 26 that sense position information relative to a transmitter 22 and transmit a position signal to the medical assistant computer where it is converted to digital form, this is not intended to be limiting.

In some cases the operating room environment can assist the position reporting sensors. For example, a metal operating table may stabilize fields when using magnetic position reporting sensors.

The medical assistant computer 21 calculates the location of the lesion based on the sensed position of the markers 26. An additional marker 27 may be located at the sternal notch of the patient. This permits calculations about movement of the sensors 26 to be made with reference to a relatively fixed point on the patient which is close to the sensors 26, which can provide for higher accuracy and better calibration.

Positional information is also determined for the surgical instrument 23, with respect to the transmitter 22. The location and position of the surgical instrument may then be determined, relative to the position of the transmitter or the markers 26 or marker 27. Thus, the position of the lesion (relative to the markers) and the position of the surgical instrument 23 (relative to the position of the markers) may be displayed on the video screen 21a of the medical assistant computer 21.

The transmitter 22 may be located anywhere relative to the patient, and may be portable as shown in FIG. 2. Preferably, the transmitter does not move during the surgical procedure. In one embodiment, the transmitter can be mounted on a pole from the ceiling, to reduce a chance that the transmitter will be bumped during the surgical procedure, causing movement of the transmitter.

Figure 3:
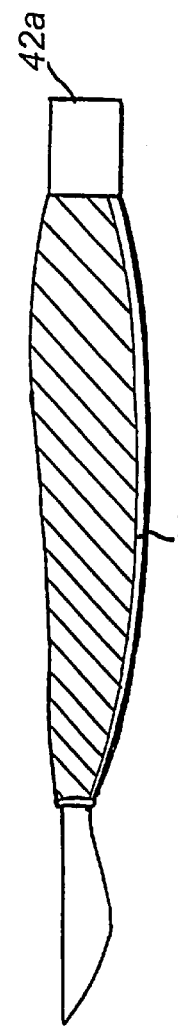
FIG. 3 illustrates one embodiment of a position-reporting sensor.

FIG. 3 illustrates one embodiment of a marker-sensor 38, that may be used for markers 26 and 27 of FIG. 2. As described above, the sensors may be position-reporting sensors. This type of sensor is known and available from Polhemus Corporation of Colchester, Vt. Another position-reporting sensor is known and available from Ascension Technology Corp., of Burlington, Vt. (e.g., Ascension's "Flock of Birds" sensors).

This type of sensor is most often found in virtual reality applications, such as gaming. The sensors may be about one-inch cubes, and may provide three or six degrees of positional information. Three degrees refers to location in the standard x, y and z Cartesian coordinate planes (relative to a receiver or transmitter 22). Six degrees of information can include these three degrees, and also pitch, roll and rotation. Smaller units, such as ¼" in diameter, may be used.

The position-reporting sensors may include a wire to provide power to the sensor or to transmit information to the medical assistant computer. In other embodiments, a battery-operated (or solar-powered) wireless sensor may be used.

The sensor may include a wireless transmitter to send the positional information to the medical assistant computer. Thus, the positional information reported by the transmitter, sensors, associated hardware and software is positional information for the sensors 26 and 27 relative to the transmitter 22.

The sensors 26 and 27 may be affixed to the skin of the patient using a medical adhesive pad 39, which are known in the art and available in a variety of sizes and shapes.

Medical position reporting sensors may be useful in other medical contexts. For example, position-reporting sensors may be affixed to a patient's chest to monitor breathing. An alarm might sound if the breathing becomes irregular or stops.

Instruments

Figure 4A:
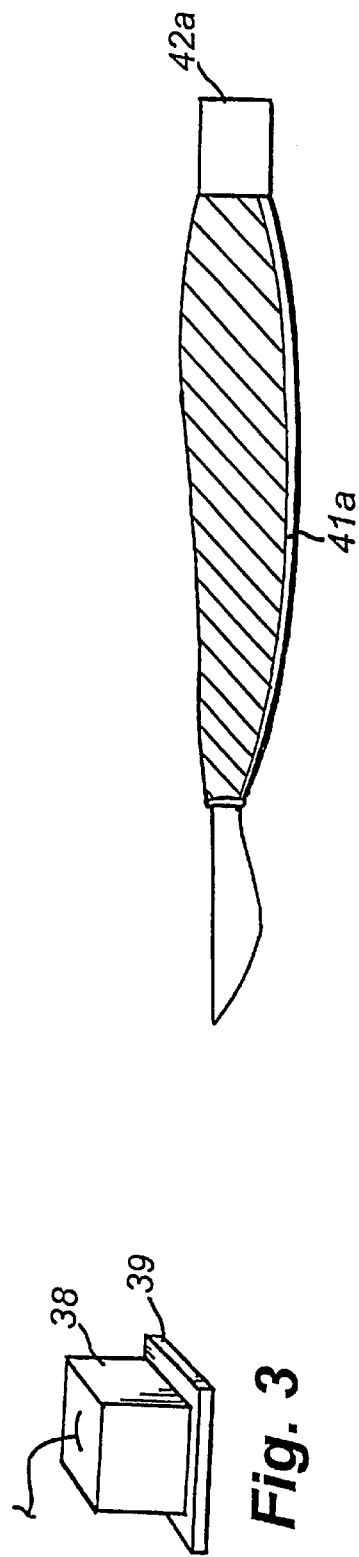
FIG. 4A illustrates one embodiment of a scalpel for use in a medical sensing and imaging system.

FIGS. 4A–4E illustrate surgical instruments adapted according to the present invention. In FIG. 4A, a scalpel 41a is illustrated. Mounted on the scalpel 41a is a sensor 42a. The sensor may be a six degree of information sensor, of the same or similar type as is used for position-reporting sensors 26 on the breast. In FIG. 4A, the sensor is illustrated as being mounted at the rear of the handle to the surgical instrument. The sensor may be affixed in other positions, for example, incorporated into the interior of the handle of the instrument.

Figure 4B:
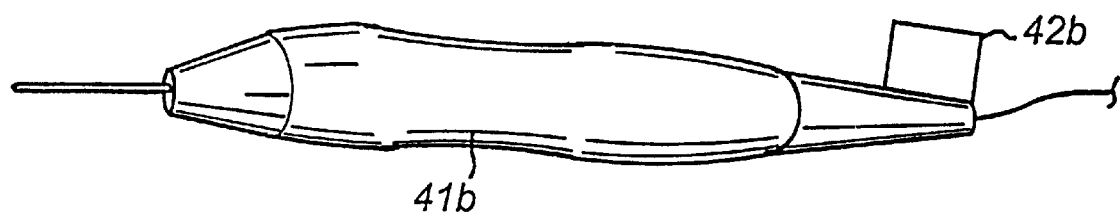
FIG. 4B illustrates one embodiment of a cauterization pen for use in a medical sensing and imaging system according to the present invention.

FIG. 4B illustrates a cauterization pen 41b. Mounted on the cauterization pen 41b is a sensor 42b, similar to that described above for the scalpel.

Figure 4C:
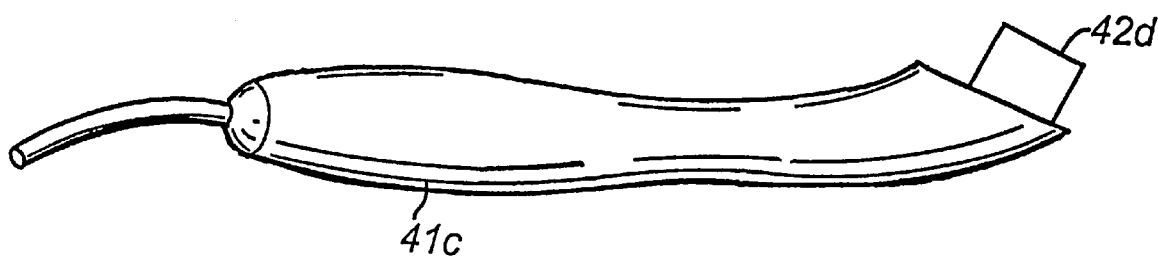
FIG. 4C illustrates one embodiment of a biopsy probe for use in the medical sensing and imaging system according to the present invention.

FIG. 4C illustrates a biopsy probe 41c, with associated sensor 42c.

Figure 4D:
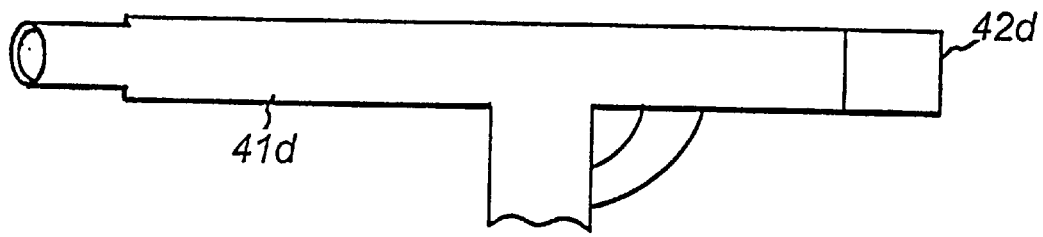
FIG. 4D illustrates one embodiment of a rotor core tool for use in a medical imaging and sensing system according to the present invention.

FIG. 4D illustrates a rotor core tool 41d including a sensor 42d.

Figure 4E:
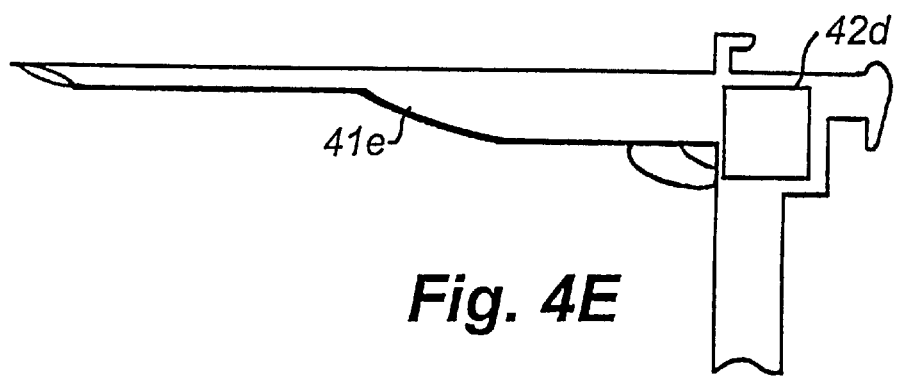
FIG. 4E illustrates one embodiment of a core biopsy gun for use in a medical imaging and sensing system according to the present invention.

FIG. 4E illustrates a core biopsy gun 41e, together with associated sensor 42e.

In an alternative embodiment, a handle can be provided that includes a position-reporting sensor. Various surgical instruments can then be attached to the handle for use in surgery.

Location of Markers

Returning to FIG. 1, step 13, the location of the markers 26 (of FIG. 2) is determined. In a preferred embodiment, three position-reporting sensors are positioned on the breast, although a different number may be used. Preferably a plurality of sensors is used, although the plurality of sensors may be incorporated into a single unit (e.g., a generally cup shaped unit that reports information as to the shape of the cup) that is fit over the breast.

At step 13, the position where the sensors should be affixed to the breast is calculated, in an effort to keep the sensors from interfering with the surgical procedure and to assure that the sensors are in a superior position to monitor movement of the breast and to determine any resulting change of location of the lesion within the breast. In one embodiment, this is achieved using the following rules for positioning of the sensors:

The sensor positions should roughly define an equilateral triangle.

The sensor positions should define a plane that passes through (or close to) the center of the lesion, the plane being parallel to the patient's chest.

The sensors should be positioned so that the point where the lesion is closest to the skin falls in the midpoint of an edge of the equilateral triangle defined by the positions of the sensors.

The last bullet point assumes that the surgical procedure will use the point where the lesion is closest to the skin as the entry point for the surgical procedure. In an alternative embodiment, the user inputs the entry point to the computer. In any event, a number of alternative factors may be used to determine automatically the location on the breast where the markers should be positioned.

Using the above principles, or otherwise, the sensor positions can be located at fixed fenestration locations, having one preset location and two calculated locations or using no predetermined locations, all of the locations being calculated for the individual patient. A location for a reference sensor, such as the sternal notch sensor, can also be selected in advance or determined for the individual patient.

In one embodiment, the medical assistant computer 21 specifies where to locate the sensors by identifying fenestration positions with respect to the first orientation of the plates for the mammography performed at step 15. When the plates are oriented in the second direction, the fenestration locations of the markers may then be observed and input to the computer (during step 16), so that the location of the lesion relative to the markers is known to the medical assistant computer for both X-rays. Thus, when the lesion location information is input to the computer with reference to the fenestration locations for both X-rays, the medical assistant computer may determine automatically the lesion location, relative to the sensors.

In an alternative embodiment, the sensors are affixed to the breast before positioning the plates for the mammography taken at step 15 of FIG. 1. In this event the location of the sensors is determined automatically or without a computer, based on a mammography and the above considerations (or others) for sensor location. If a computer is used, the medical assistant computer 21 can display an image of a breast and the location where markers should be affixed. This may be done using the imaging procedure detailed below. After the markers are attached and the mammographic plates placed in position, the user inputs to the medical assistant computer 21 the fenestration locations of each sensor with respect to each orientation of the mammography plates. This allows the medical assistant computer to determine lesion location relative to the markers, after the user inputs the fenestration readings from the X-rays.

In one embodiment, the initial position of the lesion can be determined according to the following method. The first X-ray is taken as shown in FIG. 5A. The fenestration plates 50a permit location of the lesion 52a within the breast 51a, in the z direction as shown. For the second X-ray, illustrated at FIG. 5B, the new location of the lesion in the z plane can be calculated based on the change of shape of the breast (and other factors, such as breast stiffness). This determination can be done automatically according to the methods described below with respect to a lesion modeler, approximated by an expert (as is currently done in the art) and input to the medical assistant computer or approximated by a computer based on statistical analysis. The second X-ray then permits localization of the lesion in the x and y direction, as shown in FIG. 5B. Thus, the (x, y and z) position of the lesion relative to the coordinate system established by the second position of the fenestration plates can be determined. The marker locations may also be determined or specified with respect to the second position of the fenestration plates. The relative position of the markers and the lesion, therefore, can be readily computed. When the fenestration plates are removed, the shape of the breast may change, but the sensed position of the markers on the breast will detect this, and lesion movement tracked as described below with respect to the lesion modeler.

Medical Assistant Computer

FIG. 5 illustrates a block diagram of one embodiment of a medical assistant computer. As described above, the medical assistant computer may be a general purpose computer. In this case, the block diagram of FIG. 5 shows a conceptual framework for implementation of software that performs the functions of the medical assistant computer. The software may be implemented as modules, for example, by using the C programming language for object oriented programming or other languages that are available for use with commercial computer graphics packages.

The medical assistant computer 21 receives information from the user or other components of the system at blocks 51–54. As described in greater detail below, modules 55–57 perform computations based on these inputs in order to generate an image of respective components to be displayed, e.g., the breast, lesion and instrument. An image manager 58 then coordinates each of the components 55–57. The resulting information may be displayed on a computer display 59.

Breast attributes 51 are input to the breast modeler 55 and the lesion modeler 54. Breast attributes that may be input (or automatically measured from the mammography) can include one or more of the following:

Size. This can be measured and input according to standard cup sizes.

Shape. For younger patients, the Tanner classification system may be used. For older patients, another scheme may be employed, or breast size or cup size used.

Skin thickness. This may be measured from the X-ray and input in millimeters.

Age of the patient.

Stiffness. This may be measured using a double zero durometer. The measurement reflects the malleability of the breast, the number of tendons and Cooper ligaments and collagen density of the breast. Stiffness may be used in determining lesion movement because, generally, the lower the stiffness, the more freely the lesion will move within the breast.

Areola size and number.

Expanse/symmetry. This input may reflect the size of each side of the breast, measured in centimeters, based on the two X-rays.

Chest-thoracic shape. This may be input in terms of chest-thoracic diameter and circumference. This can reflect, for example, whether the chest is of a "cave" shape or "canary" shape. A breast (and lesion within the breast) may move more freely for a cave shape chest than a canary shape chest.

As described in more detail below, these inputs can be used both for imaging the breast and for calculating movement of the lesion in response to movement of the breast.

The position of the sensors with respect to the fenestrations for the X-rays is also input, or known, to the breast modeler, this information being determined as described above. Thus, the breast modeler has the attributes of the breast and the locations of the sensors on the breast, at the time that the mammography was taken. As described in greater detail below, the breast modeler translates this information into a three-dimensional computer image of the breast for viewing by the surgeon.

As the position of the sensors changes (as indicated when coordinate reception 53 indicates a change in position), the breast modeler can change the image of the breast displayed for use by the surgeon. (In an alternative embodiment, digitized information from the X-rays may be input. This will provide at least some of the breast attribute information. In another embodiment, images of the patient's breast may be input to the breast modeler, the images of the breast being either rendered by a graphic artist or imaged using existing three-dimensional imaging technology.)

Lesion attributes 54 are input to a lesion modeler 56. The lesion attributes may include one or more of the following:

Size and shape. Various data can be input (or automatically determined from the X-ray) to show size, shape and orientation within the breast. In the embodiment described below, however, the only input is maximum diameter of the lesion in millimeters. This diameter is the greatest point to point distance across the X-rayed lesion. The system then assumes that the lesion is a sphere having the input diameter.

Calcification. This measurement reflects deposits in or near the lesion and can be determined from the mammogram.

Density of the lesion. This may be read from the opacity of the lesion in the X-ray, and classified as mild, moderate or severe.

Scarring. This may be read from the mammogram and classified into a number of levels, such as mild, moderate and severe. A further input may characterize the degree of scarring in various directions from the lesion. This may then be used in determining lesion movement because resistance to movement will be greater in the direction of greater scarring.

Hemorrhagic. Is there blood in the lesion?

Hypovascular. This may also be a yes/no input.

Inflammation/swollenness. The extent of any inflammation may be identified by physical examination, and input to the medical assistant computer. This may then be used in determining lesion movement because resistance to movement will be greater where there is inflammation.

Approximate distance from the skin surface, at closest point. This can, again, be measured from the mammogram.

Multifocality. This is the number of identifiable lesions in the breast. The above measures may be input and each lesion independently (or jointly) modeled and imaged, according to the processes described herein.

Lesion position information is also input to the computer. In one embodiment, this information is position of the lesion with respect to the fenestrations on the mammographic plates taken during the mammography, as described above. As described in greater detail below, the lesion modeler 56 generates a three-dimensional image of the lesion (e.g., a sphere), and determines its location within the breast, relative to the position of the sensors. The lesion modeler provides this information to the image manager 58 for coordinated display on the computer display 59.

In one embodiment, the lesion modeler tracks movement of the lesion as the sensors are moved during the surgical procedure. For example, if two of the sensors maintain the same position, but one of the sensors is moved closer to those two sensors, the internal position of the lesion may change. In this embodiment of the invention, that internal movement of the lesion is modeled within the computer and the change in position of the lesion is determined by the lesion modeler 56. The display on the computer display 59 can then be updated appropriately by the image manager 58. This will permit more accurate localization of the lesion for biopsy or removal.

The instrument navigator 57 translates instrument coordinate data from the position sensor or sensors located on the instrument. The instrument navigator may include three-dimensional images of each type of instrument for which the medical assistant may be used. Examples of instruments that may be used with the system include the following: scalpel, cauterization pen, biopsy tool, surgical probe, diagnostic wand (light or radiation detector based), rotor coring tool, needle coring tool and a J hook localization needle. Because the sensor may be attached to the instrument in a fixed position, the position of the sensor can be translated into the appropriate image and orientation of the instrument.

The image manager 58 receives the data from the breast modeler 55, lesion modeler 56 and instrument navigator 57 to produce a coordinated three-dimensional image. Based on the disclosure provided herein, the image manager may be readily implemented using existing software components such as those available in the WorldToolKit Library, available from SENSE8 Corp., Mill Valley, Calif. Such software can also be used to generate any field of view of the images, in response to input from the user. Finally, the image manager produces the proper display to be shown on computer display 59.

Breast Modeler 55

FIG. 6 illustrates a block diagram of one embodiment of a process that implements the breast modeler.

At step 61, an image library is formed. The image library consists of a set of images of breasts of various shapes, sizes and other attributes (as described above). The "images" may be stored as three dimensional models. One or more two dimensional overlays may be used to augment image construction, as would be apparent to one skilled in the computer graphics arts based on the disclosure provided herein. The image library may be formed in advance of examination of the patient. For example, digital images (and three dimensional models) of the breasts of cadavers or of living women may be generated. This can be done either through digital imaging or through rendition by a graphic artist. Preferably, in each case, a three-dimensional computer image of the breast is defined and stored in the breast image library (stored, e.g., as a three-dimensional model). Formation and manipulation of such three-dimensional images is well known in the art. For example, the program available from SENSE8, described above, provides for digitization of real world objects into three-dimensional computer images, manipulation of those images as solid or wire frame objects (wire frames may be used in a preferred embodiment for the image of the exterior of the breast), and accepting three-dimensional coordinate data and translating movement in that three-dimensional coordinate data to changes in the shape of an object.

The breast image library may include images of a breast both when a subject is standing upright and when the subject is in the position for which the procedure will be performed. For example, if the procedure is a lumpectomy and the patient will be lying on her back during the lumpectomy, the image library may include images of breasts of women lying on their backs. The library may further include figures associated with each breast image of breast attributes (e.g., size, shape, and other attributes described above).

At step 62, the attributes for the patient are input to the computer. At step 43, the attributes of the patient's breasts and the attributes of the stored image library of breasts are compared and a best fit image is selected. One input may specify position of the patient, for example to indicate that an image corresponding to a prone or supine patient should be selected.

Of course, a variety of different methods may be used for selecting a best fit image. According to one embodiment, the image library includes an image for each possible combination of size and shape. The image corresponding to the patient's size and shape is then selected. Of course, more sophisticated best-fit algorithms could be implemented.

In other embodiments, the breast image can be generated according to other methods. For example, an image generated from the patient's breast can be used. The computer could also be programmed to dynamically generate an image of the patient's breast, based on the input attribute information.

At step 65, during and just before the surgical procedures to be performed, new coordinate information is continuously received and forwarded to the breast modeler. This coordinate information is for the sensors on the breast 26, and the sternal notch sensor 27, all relative to the receiver 22. At step 66, the breast modeler then computes the relative position of the sensors 26 to each other, based on their position with respect to the sternal notch sensor 27.

At step 67, it is determined whether there has been a change in the relative positions of any of the sensors 26. If not, control returns to step 65, where new coordinate information is again received.

If there is a change detected at step 67, the three-dimensional image of the breast is either altered or a different image of a breast is substituted from the breast image library. The former can be done using available three-dimensional graphic modeling programs or by constructing such a program. Such programs may use, for example, finite element analysis or spline mathematics to determine the altered shape. At step 69, the updated image is output to the image manager. The positional information is also output to the image manager. This information is the position of the breast sensors 26, relative to the sternal notch sensor 27. Thus, the displayed image can approximate the actual shape of the breast at any point in time during the surgical procedure.

In many cases, the procedure is performed relative to a lesion. Here, the surgeon's primary focus may be the lesion; the image of the breast is unnecessary or unimportant. The image of the breast may be used by the surgeon, therefore, primarily to correlate orientation of the image with the surgeon's real view of the physical breast. In this case (and others) the need to show change of shape in the breast image in response to sensor movement may not justify the added computational cost of computing changes in breast shape or altering the image of the breast during the surgical procedure.

Instrument Navigator

FIG. 7 illustrates one embodiment of a process that may be performed by the instrument navigator module 57. At step 71, an image library of instruments is formed or stored. The image library should include a three-dimensional image of each surgical instrument that may be used. The three-dimensional images may either be input by graphic artists or derived from photographic images of the instruments. While referred to as "images" stored in the image library, the image library may include instrument images stored, for example, as a three dimensional model of the instrument, and optionally one or more two-dimensional photographic images to use to overlay a three dimensional view. In most cases, formation of the image library of instruments is done in advance of the surgical procedure.

Each "image" in the library may also include a specification of the precise location where a position-reporting sensor (or other marker) is affixed to the instrument. Thus, determining the position, including orientation, of the instrument sensor relative to a sternal notch sensor 27 (or other reference point) will enable specification of the precise position (including orientation) of the surgical instrument relative to the sternal notch sensor 27, and therefore, relative to the other imaged components (e.g., the breast and the lesion).

At step 72, an instrument image is selected, based on the instrument to be used for the surgical procedure to be performed. This will typically be done at the time that the surgical procedure is to be performed.

At step 73, coordinate information is received from a position-reporting sensor that is affixed to the surgical instrument. Coordinate reception may start before the surgical procedure begins and continue throughout the surgical procedure.

At step 74, the instrument navigator determines the position of the sensor located on the surgical instrument 23, relative to a sensor located on the sternal notch of the patient 27. This permits the instrument navigator to specify the precise position in three-dimensional space of the instrument with respect to the sternal notch sensor.

At step 75, the instrument navigator determines whether the position of the instrument 23 relative to the sternal notch sensor 27 has changed from the most recent report made to the image manager. If not, the instrument navigator waits to receive new coordinate information at step 73.

If there is a change in position, at step 76, the new positional information is reported to the image manager.

Lesion Modeler

Figure 8:
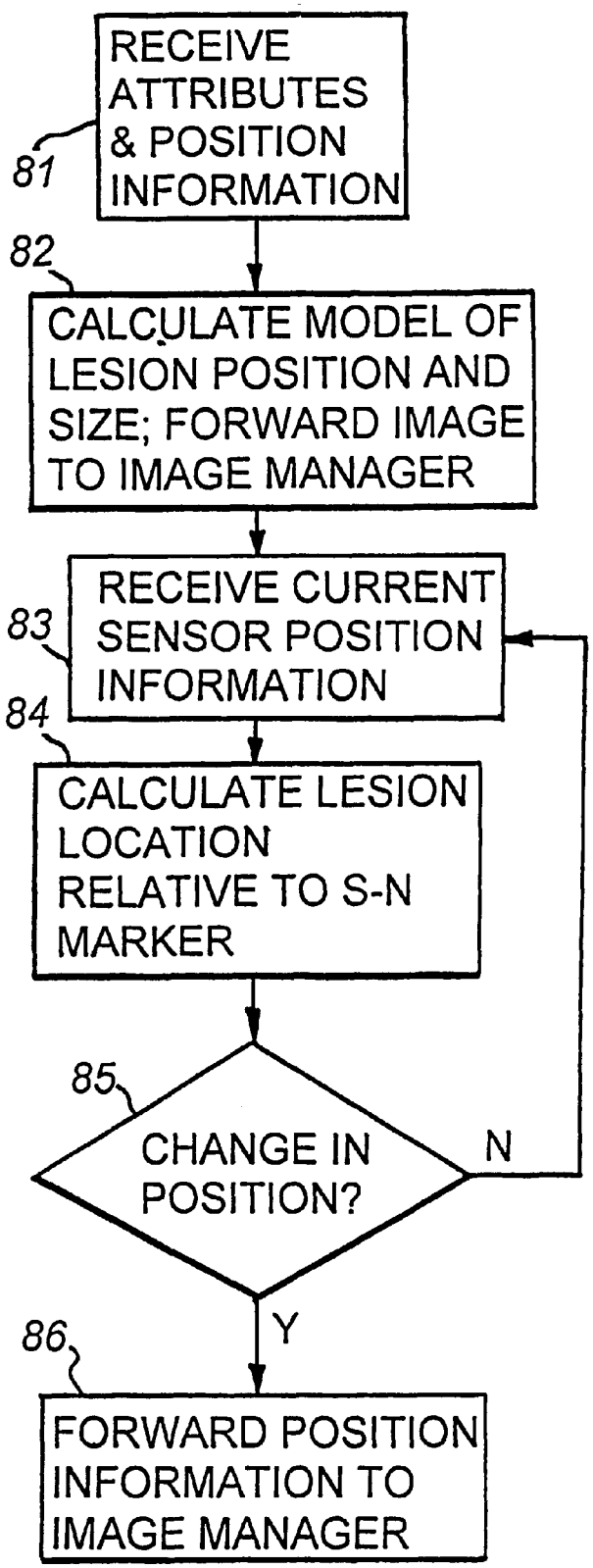
FIG. 8 illustrates one method for implementing the function of a lesion modeler in a medical assistant computer.

FIG. 8 illustrates one embodiment of a lesion modeler. The lesion modeler receives position information for the breast sensors 26 and sternal notch sensor 27 (as well as breast and lesion attribute information) and determines the position of the lesion, relative to the sternal notch sensor 27. By forwarding this positional information to the image manager, the image manager can display the current location of the lesion during surgery in correct physical location relative to the breast and surgical instrument. When the breast sensors move in a manner indicating a change in the exterior shape of the breast, the lesion modeler can detect this change and compute a new position for the lesion. Thus, the lesion modeler permits a more accurate representation of the location of the lesion as a breast moves or is manipulated during a surgical procedure.

At step 81, the lesion modeler receives breast and lesion attribute information as well as the positional information for the breast sensors 26 and the lesion position, as determined by the mammography and input according to the process described above. The breast and lesion attributes can include one or more of the breast and lesion attributes set forth above.

At step 82, the lesion modeler calculates the lesion position and size. As discussed above, the lesion size in one embodiment is determined only by the maximum diameter of the lesion. In this case, a three-dimensional image of a sphere, having such diameter, is generated and forwarded to the image manager to be used as the three-dimensional image of the lesion. Of course, more sophisticated imaging of a lesion could be done. Such imaging could allow, for example, for irregularly shaped lesions and include position information for the lesion, including orientation information.

At step 82, as described above, the lesion location relative to the sensor markers is determined from the positional data derived from the two mammography X-rays and input to the medical assistant computer.

At step 83, current sensor position information is received. This will include data for the breast sensors 26 and the sternal notch sensor 27.

At step 84, the lesion modeler calculates the lesion location, relative to the sternal notch marker 27. This is done by computing the position of the breast sensor markers 26 relative to each other and to the sternal notch sensor 27.

A variety of methods, having various degrees of sophistication, can be used to determine lesion location in response to changes in the positions of the breast sensors. For example, clinical studies or cadaver studies could be performed to empirically derive this data.

In one embodiment, lesion location may be computed as follows. In this embodiment, there are three breast sensors 26. Further, in this embodiment, the sensors are located on the breast so that the sensors define a plane in which the center of the lesion is located. This plane is also approximately parallel to the chest of the patient.

In this embodiment, the lesion location process approximates lesion location by assuming that the lesion will remain in a plane defined by the three sensors (or, in the event that the lesion modeler determines that the lesion is offset from the plane defined by the breast sensor, then assuming that the lesion will remain in a location that is offset by the same amount as the original offset). Given this assumption, lesion location and three-dimensional space has been reduced to a determination of where, in the two-dimensional plane defined by the three sensors, the lesion is located—as the sensors move, the plane moves and the calculated two-dimensional plane in which the lesion is located moves.

Identifying where in the two-dimensional plane the lesion is located can be performed according to a variety of methods, apparent to one of skill in the art based on the disclosure provided herein. In one embodiment, two-dimensional localization can be done by modeling movement in plane as a flow of fluid in the plane.

A number of variations and improvements to the above method of lesion location determination can be implemented. For example, if it is detected that the lesion is offset from the plane defined by the breast sensors, and all three of the breast sensors become closer together, the offset of the lesion from that plane may be increased. Informally, this would correspond to the case where the breast is pinched together at the sensors. In this circumstance, the offset from the plane may be increased (like squeezing a balloon, the interior materials move away from the compressed point). Similarly, if it is detected that the breast sensors move further apart, the offset of the lesion from the plane defined by the sensors may be reduced.

In another embodiment, location of the lesion relative to the breast sensors 26 can be performed using finite element analysis. Finite element analysis is known generally, and could be applied to modeling of lesion location, based on the disclosure provided herein. Using this approach, the breast is modeled as a finite number of points having certain defined relations among the points. As certain of the points move (i.e., points corresponding to breast sensors 26), the location of other points (e.g., the center of the lesion) can be calculated using the defined relations among the points. Based on the considerations described above, the input breast and lesion attribute information can be used to adjust the finite element analysis model to more accurately track lesion movement given characteristics of the particular patient's breast.

In another embodiment, known spline mathematics concepts can be used to model movement of points (e.g., the lesion) within the breast. For example, a series of splines may be calculated based on initial sensor positions and lesion position. Later movement of the sensors (e.g., changes in position and/or orientation) can then be modeled by performing calculations corresponding to the new sensor location information and based on the initial splines, to produce new splines. The new position of the lesion can then be determined from the new splines. A number of different parameters may be used in creating such a spline model. One such model is described in greater detail below.

A further description of exemplary lesion movement modelers now follows with reference to FIGS. 11–18B. As described above, such modeling may involve a two-phase approach. First, the location of the lesion is determined in a controlled setting, such as a mammography procedure. Second, the location of the lesion is predicted when the patient undergoes surgery and the breast is in a very different position.

While various techniques will be discussed for modeling the breast so as to predict the movement of the lesion and its location during surgery, only one approach (similar to the approach described with reference to FIGS. 5A and 5B), will be discussed for initially determining lesion location. Other techniques are not intended to be excluded, though.

a. Initial Lesion Localization

Initially, three or more reference surface locations (A, B, C, etc.) on the patient's breast are selected and marked. These locations may, for example, be from marks that show up on X-rays (such as the opaque markers called "bee bees"); from known locations on patient-imaging equipment (such as the positions called "cheese holes" or fenestrations on mammography equipment) which could be marked on the skin with a pen or sticky dot; or with three-dimensional (3D) tracking devices, such as the sensors described above. As described above, the sensor locations may be selected based on lesion location, as shown in a preliminary screen.

The breast is then compressed in a mammography machine, not shown in FIGS. 11–18B, as a result of which the "sides" of the breast are flat and parallel. The thickness of the breast is known from the distance between the plates of the machine. Therefore, the three dimensional (3D) position of each of the surface points can be determined accurately for a given scan. For any one scan, the lesion's location can be determined in only two dimensions (2D) (vertical and horizontal), though; its depth within the breast and along the dimension between the plates cannot be determined. However, the lesion location can be ascertained in 3D space by combining the 2D lesion position information from several scans in several directions. This is the first phase of the lesion tracking process, referred to as phase P1, for short. The procedure is somewhat similar to what the radiologist does without this invention, but instead of inserting a wire into the lesion to mark its location, as in the prior art, the radiologist instead enters the lesion's coordinates into a process that computes the lesion's 3D location from the available scan data.

FIGS. 11 and 12 (like FIGS. 5A, 5B) show the arrangements, and thus the information available from one scan. The positions of sensors S1–S3 are known in three dimensions, but the position of lesion 112 within breast 114 is known only in two dimensions. In addition to the techniques discussed relative to FIGS. 5A and 5B, by taking several scans and intersecting the lesion volumes, as stated above, the radiologist can determine the lesion's initial x, y, and z coordinates with a reasonable degree of certainty. The necessary computation is preferably automated. This computation provides the initial lesion location parameters used in the selected 3D movement model in the next phase of the process.

Once the lesion's initial reference position has been determined relative to the marked surface locations, 3D sensors S1, S2, S3 can be placed on those locations. (As described above with reference to FIG. 5A, 5B, the actual sensors can be placed before taking an X-ray. This provides another data point in monitoring changes of breast shape during the mammography procedure.) Each sensor, in this example, reports three position coordinates and three orientation coordinates. The lesion is located relative to the initial locations of the sensors.

In the second phase of the process, referred to as phase P2 for short, the patient is moved to an operating table, where the surgeon examines (e.g., a biopsy) or removes (e.g., a lumpectomy) the lesion. During this phase, the location of the lesion is predicted for the breast in a relaxed position (and continually recalculated as the breast is moved by the surgeon), relative to movement of the sensors as the breast changes shape during preparation for surgery and during the surgery itself. In addition, the surgeon's scalpel (or other instrument) preferably is tracked and its position plotted relative to the calculated position of the lesion.

During phase P2, the positions of three of the sensors S1, S2, S3 are actively tracked using position-reporting sensors and associated hardware and software, such as the Polhemus Fastrak system, as described above. This data is input to the selected lesion movement model executing in a CPU to predict the current location of the lesion. The output will be a display on a monitor, a "head's up" display worn by the surgeon or another display device. If a 2D display is used, the image may, for example, be as shown in FIG. 13. In addition, the position of the surgeon's scalpel is tracked and a representation of the scalpel 116 is displayed relative to the position of the lesion. The surgeon is able to rotate the image to any position and orientation in order to better understand the predicted (calculated) position of the lesion 112' and calculated contour 114' breast surface lesion, relative to the sensors S1–S3 and current cutting position.

b. Modeling Lesion Movement

As described above, a number of alternative approaches may be employed for modeling lesion movement. Some additional approaches will be discussed. In doing so, the expression "points are marked" refers to using any of the methods described herein for indicating initial surface locations, including sensor placement.

A more detailed overview of three modeling approaches (using a spline surface model, a linear interpolation model and a spring model) now follows:

1. Spline Surface

The location of the lesion and the marked surface points may be used to define a spline surface. The angular orientations of the sensor points are calculated during the mammography, when the sensor points are known to lie on a plane having a defined orientation substantially parallel to the patient's chest wall (because the breast is compressed by the mammography plates). When tracking devices (i.e., sensors S1–S3) are on the sensor points, the angles and positions of the sensors are used to calculate the change in the shape of the spline surface and, therefore, to calculate the new location of the lesion, it being positioned such that the spline surface, albeit with new coefficients, still passes through the sensors and the lesion. (See FIG. 13).

It is expected that this technique will work best for modeling a full, resilient breast, but that it may give poor results when the breast is loose and the surface angle is not maintained by internal structure.

In an exemplary implementation, for each of S1, S2 and S3, only the three location coordinates (x, y, z) and the tangent plane to the surface of the breast (determined as being the same as the tangent to the surface of the sensor when the sensor is attached to the breast) are used. The tangent plane is represented by a vector normal to the plane of the sensor, as shown in FIG. 18A.

This approach seems reasonable when there are no twisting torques acting on points on the breast. Other available information may be ignored, such as information about the rotation angle of the reference frame about the normal to the tangent plane; however, such information may be included in more advanced models, if desired.

In an exemplary spline surface model, the geometry of the lesion location in the breast is described with non-uniform rational Bezier splines (NURBs). The amount of data used fits the requirements for solving a geometric model based on quadratic splines (rational functions whose numerators and denominators are quadratic polynomials in "barycentric coordinates" u and v).

According to this model, sensors S1–S3 each have x, y, and z coordinates in real space (corresponding to x, y and z positions at the initialization position), and an orientation (also at the initialization position), given as the sensor's "up" vector (normal to the plane the sensor is sitting on) as described with reference to FIG. 18A. The sensor 181 has a tangent plane, indicated by arrows 183, and a normal "up" vector 182. At the lesion initialization step, the x, y, and z coordinates in real space of the lesion are also known (from the mammography, as described above).

Given these coordinates, the spline surface is set to pass through the three sensors and the lesion. The lesion's barycentric coordinates, u and v, therefore, may be determined from the x, y and z coordinates of the lesion and the sensors. As is known in the art, this is done by forming a tetrahedron using the sensors and lesion as the corners, as shown in FIG. 18B. The sum of the areas of the sides of the tetrahedron are then set to a unit value.

The lesion's x, y and z coordinates can be determined from the barycentric coordinates u, v, given a set of three equations outlined below. As described below, the equations depend on three weights. Because the initial x, y and z position of the lesion is known, the initialization position of the lesion can be used to solve the three equations for the three weights. As explained in more detail below, when the three sensors are subsequently moved, the new x, y and z position of the lesion can be determined using the already determined weights.

The lesion's position in real space is defined as a function of the lesion's barycentric coordinates, as follows.

$$O1_x(u, v) := \frac{(a_x u^2 + b_x v^2 + c_x uv + d_x u + e_x v + f_x)}{(\alpha_x u^2 + \beta_x v^2 + \gamma_x uv + \delta_x u + \epsilon_x v + \phi_x)}$$

$$O1_y(u, v) := \frac{(a_y u^2 + b_y v^2 + c_y uv + d_y u + e_y v + f_y)}{(\alpha_y u^2 + \beta_y v^2 + \gamma_y uv + \delta_y u + \epsilon_y v + \phi_y)}$$

$$O1_z(u, v) := \frac{(a_z u^2 + b_z v^2 + c_z uv + d_z u + e_z v + f_z)}{(\alpha_z u^2 + \beta_z v^2 + \gamma_z uv + \delta_z u + \epsilon_z v + \phi_z)}$$

In these equations, the x, y or z subscripts denote whether the equation refers to the x, y or z dimension of the lesion's position. Accordingly, the parameters of the lesion are defined below according to only the x dimension, with the y and z dimensions having the same definitions, but using y or z coordinates rather than x coordinates. The parameters of the $O1_x$ (u,v) equation are as follows:

$O1_x$ (u,v)=the x coordinate of the lesion in real space u and v=the barycentric coordinates of the lesion, as calculated at the initialization step (which are assumed to remain constant, even when the sensors (and, accordingly, the lesion position in real space) move)

$a_x = w_{200} * x_{200} - 2 * w_{101} * x_{101} + w_{002} * x_{002}$
$b_x = w_{020} * x_{020} - 2 * w_{011} * x_{011} + w_{002} * x_{002}$
$c_x = 2 * w_{110} * x_{110} - 2 * w_{101} * x_{101} - 2 * w_{011} * x_{011} + 2 * w_{002} * x_{002}$
$d_x = 2 * w_{101} * x_{101} - 2 * w_{002} * x_{002}$
$e_x = 2 * w_{011} * x_{011} - 2 * w_{002} * x_{002}$
$f_x = w_{002} * x_{002}$
$\alpha_x = w_{200} - 2 * w_{101} + w_{002}$
$\beta_x = w_{020} - 2 * w_{011} + w_{002}$
$\gamma_x = 2 * w_{110} - 2 * w_{101} - 2 * w_{011} + 2 * w_{002}$
$\delta_x = 2 * w_{101} - 2 * w_{002}$
$\epsilon_x = 2 * w_{011} - 2 * w_{002}$
$\phi_x = w_{002}$ where $x_{200}$=S1 x coordinate
$x_{020}$=S2 x coordinate
$x_{002}$=S3 x coordinate
$x_{110}$=x spline coefficient for line S1–S2, which is the x coordinate of the cross product of (the center point of line S1–S2) with (the average of normals for S1 and S2)

$x_{101}$=x spline coefficient for line S1–S3 the x coordinate of the cross product of (the center point of line S1–S3) with (the average of normals for S1 and S3)

$x_{011}$=x spline coefficient for line S2–S3 the x coordinate of the cross product of (the center point of line S2–S3) with (the average of normals for S2 and S3)

$w_{110}$, $w_{101}$, $w_{011}$=The spline "weights."

$w_{200}$, $w_{020}$, $w_{002}$ are assumed to be 1, in the above equations.

Thus, by knowing the initial sensor positions/orientations and the initial lesion location, the three spline weights $w_{110}$, $w_{101}$ and $w_{011}$ can be determined by solving the above three equations. The solving of the equations can be done according to any of a number of methods, as known by one of skill in the art. Software packages, such as Macsyma, are available to assist in this process.

When the sensor positions change, the new lesion location can be calculated using the already determined weights and barycentric coordinates of the lesion. When the sensors move, the spline coefficients (e.g., $x_{110}$, $x_{101}$ and $x_{011}$) change. Accordingly, the new position of the lesion ($O1_x$ (u,v), $O1_y$ (u,v), $O1_z$ (u,v)) can be determined by again solving the above equations using the already determined weights and barycentric coordinates of the lesion, and the changed $x_{200}$, $x_{020}$, $x_{002}$, $x_{110}$, $x_{101}$, $x_{011}$ values.

2. Linear Interpolation

Figure 14:
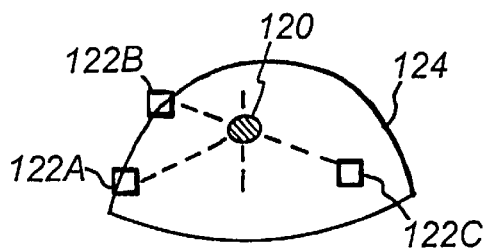
FIG. 14 illustrates use of linear interpolation to model lesion movement.

Turning to FIG. 14, the use of another modeling technique, linear interpolation, is illustrated. The relative distances between the lesion 120 and the surface points 122A–C on breast 124 are used to create a set of linear equations defining the current location of the lesion relative to the surface points. Then when the breast moves, the new surface point coordinates are used in the same set of linear equations to define the probable new lesion location. Optionally, additional information, such as the location of the chest wall, can be used to increase the accuracy of the location.

It is expected that this technique will work well for modeling a loose floppy breast, so long as additional information, such as the chest wall location, is available.

There are two directions in which a linear interpolation model requires initialization: in the sensor plane and perpendicular to the chest wall.

Figure 16:
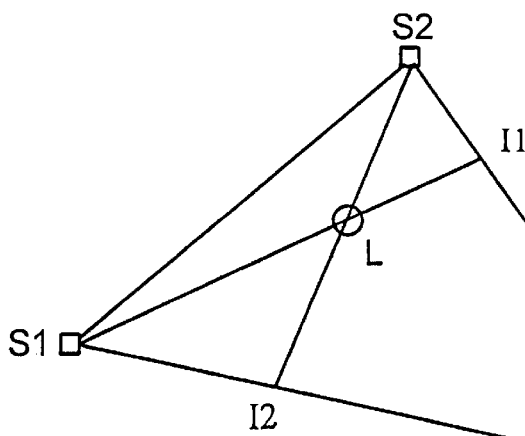
FIG. 16 illustrates an application of linear interpolation to model lesion movement.
Figure 17:
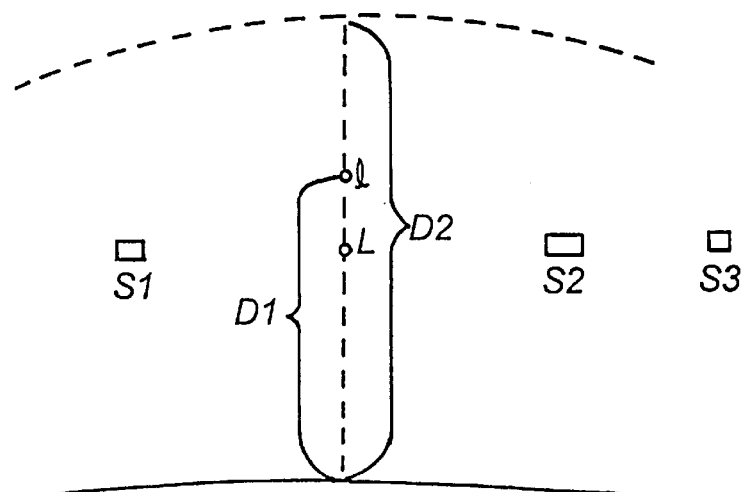
FIG. 17 illustrates use of linear interpolation to model lesion movement.

With reference to FIGS. 16 and 17 the parameters for the sensor plane are initialized as follows:

A. The lesion is projected along a perpendicular to the chest wall into the plane formed by the three sensors S1, S2, and S3. The lesion projection is at a point L in that plane.

B. A line is projected from sensor S1 through L to the line between S2 and S3. The intersection point with the line is I1.

C. A similar line is projected from sensor S2 to the line between sensors S3 and S1. The intersection point with the line S1 S3 is I2.

D. The proportion of line S2 I2 to line S2 S3 is stored, as is the proportion of line S1 I2 to S1 S3. These are the sensor plane interpolation parameters.

With reference to FIG. 17, the parameter for the interpolation perpendicular to the chest wall is calculated as follows:

A. On the mammogram, the radiologist measures the perpendicular distance from the chest CW wall to the lesion O1. This is D1.

B. The radiologist measures the perpendicular distance from the chest wall, through the lesion, to the surface of the breast. This is D2.

C. The ratio D=D1/D2 is the parameter for the interpolation perpendicular to the chest wall.

When the breast moves and the sensors are in new positions, the lesion is presumed to remain in the same relative location with respect to the sensors and the ratio D is presumed to be preserved so the change in height of the sensors relative to the chest wall is used to scale the lesion distance from the chest wall or breast surface.

3. Spring Model

Figure 15:
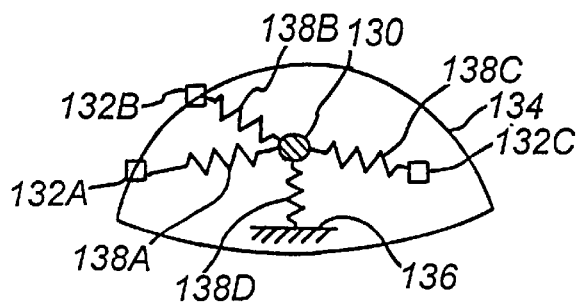
FIG. 15 illustrates use of a spring model to model lesion movement.

Another approach is to model the breast as a network of springs, one each between the lesion and a set of reference points (e.g., S1–S3). The initial positions of the lesion and surface points may be used to define parameters for a set of spring functions such that the lesion is at the common node where the springs join. That is, as illustrated in FIG. 15, it may be assumed that the lesion 130 is connected to each of the sensor points S1–S3 and the chest wall 136 via a spring 138A–138D. As the surface points move, the spring forces are recalculated to determine the new location of the lesion. This approach may be more accurate than the linear interpolation approach because it may more accurately model the dynamics of the breast tissue. Like linear interpolation, it may be supplemented with additional information, such as the location of the chest wall.

To calculate the spring constants for a spring model:

A. The radiologist measures the distance between the chest wall and the lesion and enters this (in addition to the sensor position data already entered) into the modeling software. In the alternative, this can be calculated by the medical assistant computer, which knows sensor location and lesion location.

B. The model assumes that the spring between sensor S1 and the lesion has a constant of 1.

C. The model uses a convention al differential equation solution to solve for the constants on the springs between the other two sensors and the lesion and between the chest wall and the lesion.

Note that the spring constants are based strictly on balancing theoretical forces to cause the lesion to be placed at the given location between the sensors and the chest wall. There is no attempt to model the elasticity of this particular person's breast, although additional offsets to lesion position calculated using the spring model may be included, based on breast attributes.

As changes in sensor position are detected, new lesion position can be readily determined, based on the already-determined spring constants, by solving the set of equations which finds the balanced-force position of the lesion node.

4. Combination and Enhancements

Because the dynamics of different breasts vary widely from firm and resilient to loose and floppy, the concurrent or alternative use of several such modeling techniques may be desirable, each being most applicable to a specific type of breast. The lesion location using each method may be calculated, and the new location determined by a veraging the results. The averaging process may also be weighted, based on breast attributes, to favor models found more suitable for those attributes.

Application of additional constraints may be useful, also, to increase the accuracy of the modeling process. For instance, locating a lesion in a very loose breast may be improved if the breast is first pulled taught and taped in order to ensure that the function accurately describes where the lesion is. However, it is also possible that none of these techniques will work well for extreme cases (e.g., very small or very large breasts).

In formulating the above finite element analysis, spline mathematics, spring and other models, an artificial breast may be used to measure lesion movement relative to movement of the exterior of the breast, for various size and shaped breasts and breasts having varying stiffness and varying uniformity. An artificial breast can be prepared using a latex "skin" and Agarose interior. The stiffness of the Agarose interior can be readily adjusted as known in the art to model the lesion, inflammation and breasts of varying stiffness. The particular lesion movement model can then be verified by in vivo testing.

The lesion location determination method may also be improved using the breast and lesion attribute information described above. For example, if there is significant scarring at one side of the lesion, then any calculated movement of the lesion in that direction could be discounted to reflect decreased mobility of the lesion in the direction of scar tissue. Other variations in the computation based on the breast attributes and lesion attributes described above would be readily apparent to one of skill in the art, based on the disclosure provided herein. Further modifications to the above lesion localization methods may also become apparent from clinical or cadaver studies.

Such models of lesion movement, and verification and adjustment of the models, can be implemented by one of skill in the art of medical imaging, graphics and mathematics and medical system design, based on the disclosure provided herein.

Referring to step 82, the initial position of the lesion is calculated from the mammography. As described above with reference to FIGS. 5A, 5B and also FIGS. 11, 12, this may involve coordinating data from two or more different X-rays. In one embodiment, one or more of the above lesion location models can be used when making the initial calculation of lesion location, to converge upon a model for lesion location relative to the markers. That is, changes in position of the breast markers 26 during the mammograms can be monitored and used in determining lesion location relative to the markers.

In any event, after the position of the lesion relative to the three breast sensors is determined, the position of the lesion relative to the sternal notch marker can be readily ascertained. At step 85, if there has been no change in this position, control is returned to step 83 where new sensor information is received. If there has been a change in position, the positional information is forwarded to the image manager, at step 86.

Image Manager

Figure 9:
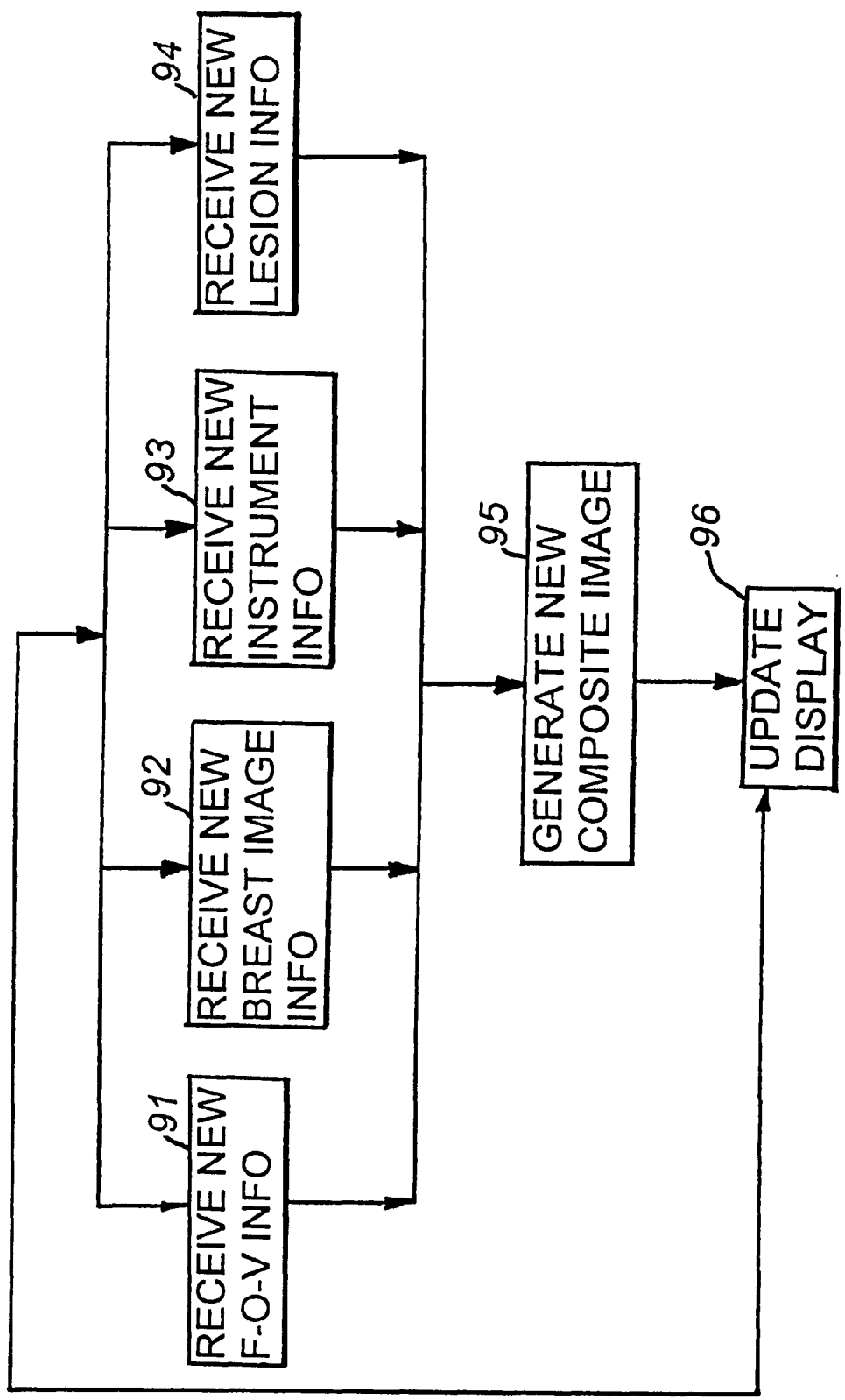
FIG. 9 illustrates one method for implementing an image manager of a medical assistant computer.

FIG. 9 illustrates operation of one embodiment of an image manager.

At steps 91–94, the image manager receives an input. For example, at step 91, the image manager may receive new information regarding the field of view that the user wishes to have displayed. At step 92, the image manager receives new information regarding the breast image or positional information for the breast, as described above. At step 93, the image manager will receive new information from the instrument navigator, as described above. At step 94, the image manager will receive new information from the lesion modeler regarding lesion location or image, as described above.

At step 95, a composite image is generated from the information received from the user, breast modeler, lesion modeler and instrument navigator. Generation of appropriate three-dimensional images and fields of view from separate three-dimensional images, given a reference point for location, is known in the art. Programs such as those available from SENSE8, discussed above, are available and may be used to accomplish this function.

The positional information is reported to the image manager with reference to the sternal notch sensor 27 of FIG. 2. The sternal notch sensor is a reference point whose position does not significantly change throughout the surgical procedure. The sensor also is relatively close to the surgical site and maintains a position relatively constant with respect to the site of the surgical procedure, even as the patient moves. As discussed above, computations of locations of the breast sensors 26 and instrument sensor relative to the sternal notch sensor 27 are made based on the relative position of each to a receiver 22 (or transmitter, depending on the position-reporting sensor).

In another embodiment, the external reference point may be the receiver/transmitter 22 itself. Here, the sternal notch sensor 27 of FIG. 2 can be omitted. In this case, generation of the composite image would be done by the image manager with reference to positional information relative to the receiver/transmitter 22, rather than a sternal notch sensor 27.

In any event, after receiving positional information relative to a single reference point, the image manager can generate a composite image, placing each portion of the image in the appropriate location and having the appropriate orientation. Optionally, appropriate images of the breast sensors 26 may be also included in the composite image generated by the image manager.

At step 96, the display to be used during the procedure is appropriately updated, which can be performed in the same manner as for other graphical display programs, known in the art.

The view may be presented from any perspective or angle, which may be adjusted by the user. In one embodiment, the medical imaging system can display multiple different views on a display, simultaneously. For example, the medical imaging system could show separate x, y and z fields of view (e.g., front, side and top views) or a field of view (adjustable and input by the user) corresponding to the angle from which the surgeon is viewing the patient, as well as two orthogonal fields of view. The size of each view may be adjustable by the user. These functions can be readily implemented using the SENSE8 program described above and corresponding operating system software (e.g. Windows95).

In addition, the resolution within the field of view may be magnified using this type of software. For example, the procedure can begin with a large field of view (e.g., 10 cm real space to 1 cm of display) and be adjusted during the procedure to focus on an area of interest. Thus, when the surgical instrument is about to perform a delicate operation (e.g., when the instrument is near the center of a lesion for a surgical biopsy), the magnification can be increased (e.g., to 0.5 cm of real space to 1 cm of display). The magnification can be done in response to real-time user commands. In the alternative, magnification can be done automatically, by determining when the surgical instrument is closer to an area of interest and automatically magnifying the field of view (and centering it at the tip of the surgical instrument) at that time. Thus, varying levels of magnification can be set automatically, or input to the computer by a surgeon, in advance of performance of the medical procedure. The computer can continuously and automatically determine distance from the tip of the instrument to the center of the lesion and set the magnification level as a function of that distance.

In performing a surgical procedure with respect to a lesion in a breast, display of an image of the breast is optional. Display of the lesion and the instrument can be sufficient.

The sensors on the breast can be shown on the display to provide a further reference frame for the surgeon to determine how to move a surgical instrument. Each sensor can be uniquely identified on the screen. For example, each sensor might have indicia on the sensor to distinguish it from the other sensors (e.g., a red, a green and a blue sensor or a sensor with a triangle, circle or square on it). The corresponding symbol or color can also be shown on the display image of the sensor.

FIG. 19 shows a display for a procedure performed with reference to a lesion in a breast, according to one embodiment of the present invention. In this embodiment, the display shows just the sensors S1–S3 (with shapes identifying the sensors), the lesion L, and a surgical instrument I. Each object also has a corresponding shadow, S1s–S3s, Ls and Is, on a plane P below the sensors S1–S3, lesion L and instrument I images. Displaying the corresponding shadow assists a surgeon in determining the correct direction and distance to move the surgical instrument, based on the flat computer screen image. Where images are shown in each of the three dimensions, the center of the lesion is reached when each images' instrument shadow Is is lined up with the center of each lesion shadow Ls.

Targeting

Because the image manager has positional information about the instrument and the lesion, the image manager can readily detect when the operating portion of the surgical instrument (e.g., the tip of a biopsy tool) is near the center of the lesion. Thus, in a biopsy procedure, the image manager can provide a (visible or audible) signal indicating when the biopsy tool is in the best position to perform the procedure. Similarly an audible signal can be used to indicate proximity to the area of interest, e.g., a tone that gets louder or changes pitch as the center is approached and beeps when the surgical instrument is properly positioned. The same function could be achieved by changing the color of the instrument according to proximity to the area of interest. An interactive language system could also be used. For example, a surgeon could query the computer (e.g., "Where should I go?") and the computer could generate a voice command giving the surgeon instructions or positional information (e.g., "The center of the lesion is located 1 cm toward the chest cavity, and one-half centimeter toward the patient's left side, from the tip of the surgical instrument."). These could be incorporated into the system described above, based on the disclosure provided herein, by using or adapting existing software components and interfacing those components to the above described system.

In another embodiment, that portion of the surgical instrument (or of the operating portion of the surgical instrument) that intersects the image of the lesion at a particular point in time can be highlighted (for example, by changing color). Thus, a surgeon can determine whether a biopsy tool is within the lesion for biopsy, or can assure that a scalpel cuts all the way around the lesion during a lumpectomy.

In another embodiment, a signal may be provided to indicate when the surgical tool is near an area of the patient's anatomy that should be avoided. For example, a warning signal could indicate that a scalpel is getting dangerously close to a major blood vessel.

The signal may be audible, so that the surgeon becomes aware that the surgical instrument is in a certain position, even when the surgeon is not looking at the screen. An audible (or visual) signal can vary in amplitude based on proximity to the area of interest (e.g., a targeted lesion or blood vessel to be avoided), thus providing additional information to the surgeon.

For procedures where a tool needs to be positioned in a certain location within a patient, a display can provide other information about the position of the tool. For example, the display can indicate the current direction of the tool with respect to the area of interest, if the tool were slid straight into the patient, based on its current orientation.

FIG. 10A illustrates a breast 100a, lesion 101a within the breast, surgical instrument 102a such as a biopsy gun, and a corresponding display 103a indicating that the tool is currently aimed above and to the right of the lesion. The length of the arrow 104a can reflect the magnitude of the error in the direction that the tool 102a is pointed. Similarly, FIG. 10B illustrates a breast 100b, lesion 101b within the breast, surgical instrument 102b such as a biopsy gun, and a corresponding display 103b indicating that the tool is currently aimed above and to the left of the lesion. FIG. 10C corresponds to when the tool 102c is aimed directly at the center of the lesion.

Recording of Procedure

As described above, the positional information of the markers, lesion and instrument are determined and displayed by the medical assistant computer 21. Because this information is determined by the medical assistant computer, it can be stored for later retrieval and review, for example by storing positional information every tenth of a second. This can be useful for reviewing the surgical procedure for training or medical malpractice liability purposes.

Having thus described at least one illustrative embodiment of the invention, various modifications and improvements will readily occur to those skilled in the art and are intended to be within the scope of the invention. Accordingly, the foregoing description is by way of example only and is not intended as limiting. The invention is limited only as defined in the following claims and the equivalents thereto.

What is claimed is:

1. A method of monitoring a location of an area of interest within a patient during a medical procedure, the method comprising the steps of:
   affixing a plurality of markers to the skin of the patient, the markers being capable of movement relative to each other during the medical procedure;
   monitoring changes in the position of the markers relative to each other; and
   determining a new location of the area of interest by reference to the changed positions of the markers.

2. The method of claim 1, wherein the step of monitoring changes includes a step of monitoring the position of the positions of the markers relative to an external reference point.

3. The method of claim 2, further comprising the step of affixing the external reference point to the patient.

4. The method of claim 3, wherein the step of affixing the external reference point includes a step of affixing a transmitter generating a magnetic field.

5. The method of claim 1, wherein the step of affixing the plurality of markers includes a step of affixing at least one marker to a portion of the patient's anatomy that is primarily soft tissue.

6. The method of claim 5, further comprising a step of displaying an instrument to be used in the procedure, and a lesion within the portion, the display showing the relative position of the lesion and the instrument.

7. The method of claim 5, wherein the step of affixing at least one of the markers includes a step of affixing the at least one marker to the patient's breast.

8. The method of claim 5, further comprising a step of displaying an image corresponding to the portion of the patient's anatomy.

9. The method of claim 8, further comprising a step of adjusting the display to show changes of shape of the portion in response to changes in the relative positions of the markers.

10. The method of claim 9, wherein the step of adjusting includes a step of adjusting the display to show changes in the shape of a breast.

11. The method of claim 1, further comprising step of:
   displaying an instrument to be used in a procedure on a portion of the patient's anatomy; and
   displaying a lesion, the display showing the relative positions of the lesion and the instrument.

12. The method of claim 11, further comprising a step of determining the relative positions of the instrument and the lesion over time based on the changes in the position of the markers relative to each other over time.

13. The method of claim 12, wherein the step of affixing the plurality of markers includes a step of affixing a plurality of position-reporting sensors to a patient's breast.

* * * * *